United States Patent
Kemp et al.

(10) Patent No.: US 10,144,005 B2
(45) Date of Patent: Dec. 4, 2018

(54) CATALYSTS

(76) Inventors: Richard William Kemp, Derby (GB); Ronald Hage, Leiden (NL); Wei Zhao, Shanghai (CN); Jianrong Zhang, Shanghai (CN); Yong Jiang, Suzhou (CN); Hong Xie, Suzhou (CN)

(*) Notice: Subject to any disclaimer, the term of this patent is extended or adjusted under 35 U.S.C. 154(b) by 0 days.

(21) Appl. No.: 14/343,174

(22) PCT Filed: Sep. 8, 2011

(86) PCT No.: PCT/CN2011/001518
§ 371 (c)(1),
(2), (4) Date: Jun. 2, 2014

(87) PCT Pub. No.: WO2013/033864
PCT Pub. Date: Mar. 14, 2013

(65) Prior Publication Data
US 2014/0329665 A1 Nov. 6, 2014

(51) Int. Cl.
*B01J 31/26* (2006.01)
*C07F 13/00* (2006.01)
*B01J 31/22* (2006.01)

(52) U.S. Cl.
CPC ........... *B01J 31/26* (2013.01); *B01J 31/2295* (2013.01); *C07F 13/005* (2013.01); *B01J 2531/72* (2013.01)

(58) Field of Classification Search
None
See application file for complete search history.

(56) References Cited

U.S. PATENT DOCUMENTS

| | | |
|---|---|---|
| 5,153,161 A | 10/1992 | Kerschner et al. |
| 5,256,779 A | 10/1993 | Kerschner et al. |
| 5,274,147 A | 12/1993 | Kerschner et al. |
| 5,329,024 A | 7/1994 | Jureller et al. |
| 5,356,554 A | 10/1994 | Delwel et al. |
| 5,429,769 A | 7/1995 | Nicholson et al. |
| 5,516,738 A | 5/1996 | Jureller et al. |
| 5,563,201 A | 10/1996 | Joanicot et al. |
| 5,756,727 A | 5/1998 | Beller et al. |
| 6,087,312 A | 7/2000 | Masotti et al. |
| 6,432,900 B1 | 8/2002 | Appel et al. |
| 7,972,386 B2 | 7/2011 | de Almeida et al. |
| 7,976,582 B2 | 7/2011 | de Almeida et al. |
| 8,455,423 B2 | 6/2013 | Hage et al. |
| 2001/0025695 A1 | 10/2001 | Patt et al. |
| 2002/0010120 A1 | 1/2002 | Hage et al. |
| 2002/0066542 A1 | 6/2002 | Jakob et al. |
| 2002/0160925 A1 | 10/2002 | Hage et al. |
| 2003/0040459 A1 | 2/2003 | Araya et al. |
| 2005/0137105 A1 | 6/2005 | Griese et al. |
| 2005/0137118 A1 | 6/2005 | Silveri |
| 2006/0277687 A1 | 12/2006 | Buhler et al. |
| 2009/0205143 A1 | 8/2009 | Hage et al. |
| 2012/0202990 A1 | 8/2012 | Reinhardt et al. |
| 2012/0302490 A1* | 11/2012 | Reinhardt ............. C07F 13/005 510/496 |

FOREIGN PATENT DOCUMENTS

| | | | |
|---|---|---|---|
| EP | 0458397 A2 | 11/1991 | |
| EP | 0458398 A2 | 11/1991 | |
| EP | 0509787 A2 | 10/1992 | |
| EP | 0530870 A1 | 3/1993 | |
| EP | 0544490 A1 | 6/1993 | |
| EP | 0544491 A2 | 6/1993 | |
| EP | 2474578 A1 * | 7/2011 | ............... C09D 7/04 |
| JP | 2007-112761 A | 5/2007 | |
| WO | WO-1993/025562 A1 | 12/1993 | |
| WO | WO-1994/005422 A1 | 3/1994 | |
| WO | WO-1995/027773 A1 | 10/1995 | |
| WO | WO-1995/030733 A1 | 11/1995 | |
| WO | WO-96/06157 A1 | 2/1996 | |
| WO | WO-1996/006154 A1 | 2/1996 | |
| WO | WO-1997/044520 A1 | 11/1997 | |
| WO | WO-2001/064697 A1 | 9/2001 | |
| WO | WO-2001/064993 A1 | 9/2001 | |
| WO | WO-2002/064721 A1 | 8/2002 | |
| WO | WO-2002/088063 A1 | 11/2002 | |
| WO | WO-2006/125517 A1 | 11/2006 | |
| WO | 2011/032666 A1 | 3/2011 | |
| WO | WO-2011/066934 A1 | 6/2011 | |
| WO | WO-2011/066935 A2 | 6/2011 | |
| WO | WO-2011/106906 A1 | 9/2011 | |

OTHER PUBLICATIONS

Garcia-Bosch et al., "Efficient and Selective Peracetic Acid Epoxidation Catalyzed by a Robust Manganese Catalyst," *Organic Letters*, 10:2095-2098 (2008).
Gilbert et al., "Azo dye oxidation with hydrogen peroxide catalysed by manganese 1,4,7-triazacyclononane complexes in aqueous solution," *Org. Biomol. Chem.*, 1:1568-1577 (2003).
Gilbert et al., "A mechanistic study of the epoxidation of cinnamic acid by hydrogen peroxide catalysed by manganese 1,4,7-trimethyl-1,4,7-triazacyclonane complexes," *J. Mol. Catal. A*, 219(1):265-272 (2004).
Gilbert et al., "Formation and reaction of O-Mn$^V$ species in the oxidation of phenolic substrates with $H_2O_2$ catalysed by the dinuclear manganese($^{IV}$) 1,4,7-trimethyl-1,4,7-triazacyclononane complex $[Mn^{IV}_2(\mu-O)_3(TMTACN)_2](PF_6)_2$," *Org. Biomol. Chem.*, 2:1176-1180 (2004).
Hage et al., "Efficient manganese catalysts for low-temperature bleaching," *Nature*, 369:637-639 (1994).
Koek et al., "Improved syntheses, structures, spectral and electrochemical properties of $[Mn^{III}_2(\mu-O)2_cMe)_2L_2]^{2+}$ and $[Mn^{IV}_2(\mu-O)_3L_2]^{2+}$ complexes. Two homologous series derived from eight N-substituted 1,4,7-triazacyclonanes," *J. Chem. Soc., Dalton Trans.*, pp. 353-362 (1996).
Koek et al., "Synthesis and properties of hydrophobic [MnIV2 $(\mu-O)_3(L)2]^{2+}$ complexes, derived from alkyl substituted 1,4,7-triazacyclonane ligands," *Inorganica Chimica Acta*, 295:189-199 (1999).

(Continued)

*Primary Examiner* — Yun Qian
(74) *Attorney, Agent, or Firm* — McCarter & English, LLP; Yu Lu

(57) ABSTRACT

The present invention concerns the synthesis of dry powdered manganese complexes using spray-drying or freeze-drying methods.

27 Claims, No Drawings

(56) References Cited

OTHER PUBLICATIONS

Reinhardt, "Fingerprints of bleach systems," *J. Mol. Catal. A: Chemical*, 251:177-184 (2006).

Romakh et al., "Dinuclear manganese complexes containing 1,4,7-dimethyl-1,4,7-triazacyclonane ligands as well as carboxylato and oxo bridges," *Inorganica Chimica Acta*, 359:1619-1626 (2006).

Schäfer et al., "Electronic Structure of Antiferromagnetically Coupled Dinuclear Manganse ($Mn^{III}Mn^{IV}$) Complexes Studied by Magnetic Resonance Techniques," *J. Am. Chem. Soc.*, 120:13104-13120 (1998).

Wieghardt et al., "Assembly and Structural Characterization of Binuclear μ-Oxo-di-μ-acetato Bridged Complexes of Manganese($_{III}$). Analogues of the Di-iron($_{III}$) Centre in Hemerythrin," *J. Chem. Soc. Chem. Commun.*, pp. 347-349 (1985).

Wieghardt et al., "Synthesis, Crystal Structures, Reactivity, and Magnetochemistry of a Series of Binuclear Complexes of Manganese(II), -(III), and -(IV) of Biological Relevance. The Crystal Structure of [L '$Mn^{IV}$($_{μ}$-O)$_3Mn^{IV}$L'](PF$_6$)$_2$•H$_2$O Containing an Unprecedented Short Mn•••Mn distance of 2.296 Å," *J. Am. Chem. Soc.*, 110:7398-7411 (1988).

Wieprecht et al., "Terpyridine-Manganese Complexes: A New class of Bleach Catalysts for Detergent Applications," *J. Surfactants and Detergents*, 7(1):59-66 (2004).

JP 2007-112761 English Abstract.

\* cited by examiner

CATALYSTS

REFERENCE TO RELATED APPLICATIONS

This application is a U.S. National Stage Application filed under 35 U.S.C. 371, based on International Application No. PCT/CN2011/001518, filed on Sep. 8, 2011, the entire content of which is incorporated herein by reference.

FIELD

The invention concerns the synthesis of dry manganese ion-containing catalysts and dry manganese ion-containing catalysts, suitable for use in bleaching and other oxidative methods. These may, for example, be prepared using spray-drying or freeze-drying methods. Prior to drying, the catalysts may be synthesised in aqueous or non-aqueous solutions.

BACKGROUND

Wieghardt et al., in *J. Am. Chem. Soc.*, 110, 7398 (1988) describe the synthesis of $[Mn^{IV}{}_2(\mu\text{-}O)_3(Me_3\text{-TACN})_2](PF_6)_2$ ($Me_3$-TACN=1,4,7-trimethyl-1,4,7-triazacyclononane) as solid materials by precipitation of the compounds containing the large non-coordinating $PF_6$ counterion. The $[Mn^{IV}{}_2(\mu\text{-}O)_3(Me_3\text{-TACN})_2](PF_6)_2$ is prepared by reacting a dinuclear bis-carboxylate bridged $Me_3$-TACN manganese (III) complex in ethanol/water mixture and air (dioxygen).

Wieghardt et al., in *J. Am. Chem. Soc*, 120, 13104 (1998) describe the synthesis of $[Mn^{IV}Mn^{III}(\mu\text{-}O)_2(\mu\text{-}OAc)(Me_4\text{-DTNE})](ClO_4)_2$ and $[Mn^{IV}Mn^{III}(\mu\text{-}O)_2(\mu\text{-}OAc)(Me_4\text{-DTNE})](BPh_4)_2$ ($Me_4$-DTNE=1,2-bis-(4,7-dimethyl-1,4,7-triazacyclonon-1-yl)-ethane and $BPh_4$ is tetraphenylborate) as solid materials by precipitation of the compounds containing large non-coordinating counterions. The $[Mn^{IV}Mn^{III}(\mu\text{-}O)_2(\mu\text{-}OAc)(Me_4\text{-DTNE})](ClO_4)_2$ is prepared by reacting Mn(III) acetate in methanol and allowing slow aerial oxidation to form the complex.

Koek et al., in *Inorg. Chim. Acta*, 295, 189 (1999) describe the synthesis of dinuclear Mn(IV) complexes based on TACN derivatives as hexafluorophosphate salts using water/ethanol mixtures.

WO 96/06154 describes the synthesis of $[Mn^{IV}Mn^{III}(\mu\text{-}O)_2(\mu\text{-}OAc)(Me_4\text{-DTNE})](PF_6)_2$ by reacting Mn(II) acetate tetrahydrate in ethanol/water in the presence of $KPF_6$, after which hydrogen peroxide/NaOH was added and subsequently neutralised using acetic acid.

WO 2006/125517 discloses the preparation in aqueous media and use of manganese complexes with $Me_3$-TACN and $Me_4$-DTNE as highly water-soluble salts in bleaching. The complexes were prepared in situ and were not isolated as solid materials.

U.S. Pat. No. 5,274,147, to Unilever, discloses the formation of tri-μ-oxo bridged manganese complexes containing $Me_3$-TACN carried by treatment of dinuclear bis-carboxylate bridged complexes in aqueous ethanol solutions, to yield $PF_6$ or perchlorate salt complexes.

U.S. Pat. No. 5,153,161, to Unilever, discloses the formation of tri-μ-oxo bridged manganese complexes as $PF_6$ salts containing $Me_3$-TACN obtained by treatment of aqueous solutions of ligand with manganese salts and hydrogen peroxide.

U.S. Pat. No. 5,256,779, to Unilever, discloses the formation of tri-μ-oxo bridged manganese complexes containing $Me_3$-TACN obtained by treatment of aqueous solutions of ligand with manganese salts and hydrogen peroxide.

WO 2011/032666, to Clariant, describes the synthesis of dinuclear manganese and iron complexes containing $Me_3$-TACN or $Me_4$-DTNE as $PF_6$, perchlorate or tetraphenylborate salts by using only water in the synthetic procedures.

WO 2011/066934 and WO2011/066935, both to Clariant, describe the synthesis of dinuclear manganese complexes containing $Me_3$-TACN or $Me_4$-DTNE as tosylate salts, yielding non-hygroscopic solid complexes.

Manganese ion-containing complexes, typically dinuclear manganese ion-containing complexes, comprising $Mn^{III}$ and/or $Mn^{IV}$ ions and ligands based upon triazacyclononane (e.g. $Me_3$-TACN), are typically formed by allowing manganese salts (often $Mn^{II}$ salts) to react with the triazacyclononane-based ligand in aqueous solvents under inert conditions (e.g. nitrogen or argon atmosphere), after which hydrogen peroxide is usually added to form catalytically active high-valent $Mn^{III}$ and/or $Mn^{IV}$ species.

Isolation of salts of manganese complexes comprising, for example, $Me_3$-TACN or $Me_4$-DTNE ligands, and which are poorly water-soluble, such as the $PF_6$, $ClO_4$, tetraphenylborate and tosylate salts, from aqueous solution is straightforward, as is shown in the prior art. However, the isolation of salts of complexes comprising non-coordinating ions that make the complexes highly water-soluble, for example chloride, acetate, benzoate, sulfate or nitrate, is problematic: it is difficult to remove the water without causing decomposition of the complexes when performed under reduced pressure or at higher temperatures.

SUMMARY

We have found that, by carrying out the complexation (in which manganese salts (often as $Mn^{II}$ salts) react with ligand(s) in solvent) in a non-aqueous or substantially non-aqueous solvents, whereby to address the aforementioned disadvantages associated with complexation in aqueous solutions, evaporation of the solvent can be achieved under reasonably mild conditions. In this way, undesirable decomposition of the resultant complexes can be avoided. However, the use of such solvents limits the scope of complexation procedures and solvent systems for these. Furthermore, safety and environmental concerns mean that it is not always desirable to use volatile solvents, since these contribute to emission of volatile organic compounds.

We have surprisingly found that, when using spray-drying or freeze-drying methods to obtain solid salts of manganese complexes, the resultant manganese catalyst salts show a high degree of storage stability. In other words, we have found that these methods of drying do not lead to excessive decomposition of the manganese complexes. This finding is particularly useful in (although is not limited to) the synthesis of highly-water soluble manganese ion-containing transition-metal salt complexes, such as those described in WO 2006/125517 A1. Moreover, this finding is also advantageous in spray-drying aqueous mixtures of catalysts that have not been made by complexation in substantially non-aqueous solvents, since spray-drying aqueous mixtures can be preferable on account of safety concerns.

Moreover, we have found that, when solid manganese catalysts contain significant amounts of water, their stabilities on storage were, unexpectedly, worse than those of carefully dried materials. In particular, preformed transition metal catalyst salts such as those described herein, wherein the transition metal catalyst salt has been spray- and/or freeze-dried, are suitable for storage, and may thus be stored, for example in a closed, preferably sealed, container, typically under an inert gas such as argon or nitrogen. We have found that spray- and/or freeze-dried compositions of manganese catalysts are typically stable at 30° C. for at least 4 weeks. This is surprising since the same catalysts are known to be functional as bleaching catalysts in aqueous media and it is counterintuitive for stability to increase in the presence of decreased amounts of water in dried samples.

Our finding shows that spray- and/or freeze-drying materials avoids excessive decomposition and is thus of benefit in order to obtain samples of desirable degrees of purity, and which are storage-stable. In particular, it is now found that using spray- or freeze-drying to obtain solid salts containing a water concentration of less than 14 wt %, the manganese catalysts salts show good storage stability.

Viewed from a first aspect, therefore, the invention provides a method of preparing a powder comprising a manganese transition metal catalyst of a ligand of formula (I):

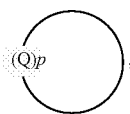

(I)

(wherein:

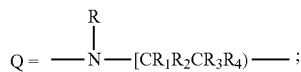

p is 3;
R is independently selected from: hydrogen, C1-C6-alkyl, C2OH, C1COOH, and pyridin-2-ylmethyl or one of R is linked to the N of another Q from another ring via an ethylene or a propylene bridge; and
R1, R2, R3, and R4 are independently selected from: H, C1-C4-alkyl, and C1-C4-alkylhydroxy) and less than 14 wt % of water, for example less than 12 wt % water, the method comprising spray-drying or freeze-drying a mixture comprising the catalyst.

Viewed from a second aspect, the invention provides a powder comprising a manganese transition metal catalyst of a ligand of formula (I):

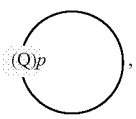

(I)

(wherein:

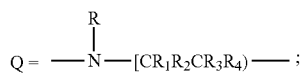

p is 3;
R is independently selected from: hydrogen, C1-C6-alkyl, C2OH, C1COOH, and pyridin-2-ylmethyl or one of R is linked to the N of another Q from another ring via an ethylene or a propylene bridge; and
R1, R2, R3, and R4 are independently selected from: H, C1-C4-alkyl, and C1-C4-alkylhydroxy) and less than 14 wt % of water, for example less than 12 wt % water.

Further aspects and embodiments of the present invention will be evident from the discussion that follows below.

DETAILED DESCRIPTION

The present invention is based in part on the finding that spray- and/or freeze-drying may be used to provide solid forms of salts of manganese complexes, which show a high degree of storage stability.

According to particular embodiments of both aspects of the invention, each R in the ligands of formula (I) is independently selected from: $CH_3$, $C_2H_5$, $CH_2CH_2OH$ and $CH_2COOH$. According to particular embodiments of both aspects of the invention, each of these and the other possibilities for R is the same. According to particular embodiments each R is $CH_3$.

According to particular embodiments of both aspects of the invention, R1, R2, R3, and R4 in the ligands of formula (I) are independently selected from: H and Me.

When a catalyst of a ligand of formula (I) comprises one group R linked to the N of another Q from another ring via an ethylene or propylene bridge, it will be understood that such ligands of formula (I) may alternatively be represented by the following structure:

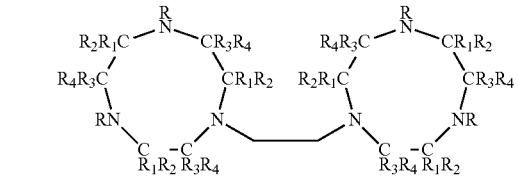

and a homologous structure having a propylene bridge between the two rings, wherein R, R1, R2, R3, and R4 are as herein defined. When a catalyst of a ligand of formula (I) comprises one group R linked to the N of another Q from another ring via an ethylene or propylene bridge, this is typically an ethylene bridge.

The preferred ligands of the transition metal catalyst are 1,4,7-trimethyl-1,4,7-triazacyclononane ($Me_3$-TACN) and 1,2-bis-(4,7-dimethyl-1,4,7-triazacyclonon-1-yl)-ethane ($Me_4$-DTNE).

The manganese complexes referred to herein are typically complexes of one or more ligands of formula (I) comprising one or two manganese ions, typically two manganese ions. Preferably the manganese complex is dinuclear and is of the oxidation states selected from II-II, III-III, III-IV, and IV-IV. The manganese ions are generally Mn(III) and/or Mn(IV). For example, in complexes comprising two manganese ions, these typically comprise two Mn(III) ions, two Mn(IV) ions or one Mn(III) ion and one Mn(IV) ion. Typical complexes comprise two Mn(IV) ions or one Mn(III) ion and one Mn(IV) ion.

The complexes comprise coordinating and non-coordinating counterions.

Co-ordinating counterions for the transition metal complexes are generally $O^{2-}$ and/or carboxylate (e.g. acetate) bridges. Typically, the transition metal complexes comprise one or more $O^{2-}$ or carboxylate (e.g. acetate) bridges including at least one $O^{2-}$ co-ordinating bridge. In particular, where the ligand of formula (I) is $Me_3$-TACN (or another ligand of formula (I) in which no R group is linked to the N of another Q from another ring via an ethylene or propylene bridge) either (i) three $O^{2-}$ co-ordinating counterions or (ii) one $O^{2-}$ co-ordinating counterion and two carboxylate coordinating counterions are typical, with acetate moieties typically being the co-ordinating carboxylate counterions where these are present. Where the ligand of formula (I) is Me$_4$-DTNE (or another ligand of formula (I) comprising one R group linked to the N of another Q from another ring via an ethylene or propylene bridge) the coordinating counterions are typically two O$^{2-}$ ions and one carboxylate ion, with an acetate moiety being a typical carboxylate coordinating counterion.

Typically, but not necessarily, the ligand of formula (I) is 1,4,7-trimethyl-1,4,7-triazacyclononane (Me$_3$-TACN) or 1,2-bis-(4,7-dimethyl-1,4,7-triazacyclonon-1-yl)-ethane (Me$_4$-DTNE). Typically, where a complex comprises Me$_3$-TACN (or another ligand of formula (I) in which no R group is linked to the N of another Q from another ring via an ethylene or propylene bridge), this comprises two Me$_3$-TACN ligands and two manganese ions, generally Mn(III) and/or Mn(IV) ions.

With Me$_3$-TACN (or other ligands of formula (I) in which no R group is linked to the N of another Q from another ring via an ethylene or propylene bridge), dinuclear Mn(IV)Mn(IV) complexes are preferred. With Me$_4$-DTNE (or other ligands of formula (I) comprising one R group linked to the N of another Q from another ring via an ethylene or propylene bridge), dinuclear Mn(III)Mn(IV) complexes are preferred. For example, the transition metal catalyst according to particular embodiments of both aspects of the invention may be a salt of the metal complexes [(Mn$^{IV}$)$_2$(µ-O)$_3$(Me$_3$-TACN)$_2$]$^{2+}$, [(Mn$^{III}$)$_2$(µ-O)(µ-CH$_3$COO)$_2$(Me$_3$-TACN)$_2$)]$^{2+}$ or [Mn$^{III}$Mn$^{IV}$(µ-O)$_2$(µ-CH$_3$COO)(Me$_4$-DTNE)]$^{2+}$.

The non-coordinating anion of the transition metal catalyst salt is not particularly limited: for example, this may be selected from the group consisting of chloride, acetate, benzoate, sulfate, tosylate, nitrate, perchlorate, and hexafluorophosphate.

The invention is, however, particularly advantageous with regard to the provision of highly water-soluble salts of complexes, for example those having a solubility (in water at 20° C.) of at least 30 g/l, such as chloride, bromide, sulfate, acetate, benzoate and nitrate. Most preferred are the manganese complexes having non-coordinating anions selected from chloride and sulfate.

The invention is particularly useful with regard to the provision of the following manganese ion-containing catalyst salts: [(Mn$^{IV}$)$_2$(µ-O)$_3$(Me$_3$-TACN)$_2$]SO$_4$, [Mn$^{III}$Mn$^{IV}$(µ-O)$_2$(µ-CH$_3$COO)(Me$_4$-DTNE)]Cl$_2$, [(Mn$^{IV}$)$_2$(µ-O)$_3$(Me$_3$-TACN)$_2$](CH$_3$COO)$_2$, [(Mn$^{IV}$)$_2$(µ-O)$_3$(Me$_3$-TACN)$_2$](NO$_3$)$_2$ and [Mn$^{III}$Mn$^{IV}$(µ-O)$_2$(µ-CH$_3$COO)(Me$_4$-DTNE)](NO$_3$)$_2$. According to particular embodiments of both aspects of the invention the catalyst salt is [(Mn$^{IV}$)$_2$(µ-O)$_3$(Me$_3$-TACN)$_2$]SO$_4$. According to other embodiments of both aspects of the invention, the catalyst salt is [Mn$^{III}$Mn$^{IV}$(µ-O)$_2$(µ-CH$_3$COO)(Me$_4$-DTNE)]Cl$_2$, Before drying, synthesis of a complex of the manganese transition metal catalyst of the ligand of formula (I) may be effected. This may be achieved according to any convenient method. For example, manganese catalyst salts, for example dinuclear manganese catalyst salts (dinuclear referring to the presence of two manganese ions within the same complex), may be formed from a ligand of formula (I) as defined herein by:
(i) contacting a 0.03 mmol/ml to 4 mmol/ml solution of the ligand of formula (I) in a solvent with a manganese salt to form a complexation mixture, wherein the ratio of macrocyclic rings in the ligand of formula (I) comprising three backbone nitrogen atoms to manganese ions of a manganese salt is from 0.8:2 and the complexation mixture contains from 0 to 6 wt % of water;
(ii) treating the solution resultant from (i) with hydrogen peroxide or a source of hydrogen peroxide to provide from 1 to 10 mole H$_2$O$_2$ per mole of the manganese salt;
(iii) treating the solution resultant from (ii) with base to provide a solution having a pH of from 8 to 13; and
(iv) treating the solution resultant from (iii) with acid to provide a solution having a pH of from 4 to 9.

By "the ratio of macrocyclic rings in the ligand of formula (I) comprising three backbone nitrogen atoms to manganese ions of a manganese salt" is meant the ratio of the cyclic Q$_3$ moieties in the ligand of formula (I) to the manganese ions of the manganese salt. Thus, when a ligand of formula (I) comprises one R group linked to the N of another Q from another ring via an ethylene or propylene bridge, such ligands comprise two cyclic Q$_3$ moieties; and when a ligand of formula (I) does not comprise a R group linked to the N of another Q from another ring via an ethylene or propylene bridge, such ligands comprise one cyclic Q$_3$ moiety. The ratio referred to in (i) above refers to the molar ratio of cyclic Q$_3$ moieties in the ligand of formula (I) to manganese ions of the manganese salt with which the ligand of formula (I) is contacted.

In such synthetic methods, in which the complexation mixture contains from 0 to 6 wt % water (herein comprising "a non-aqueous complexation method"), it is typical for the mixture, typically a solution, after completion of step (iv) to comprise no more than 20 vol % water, such as from 0 to 20 vol % water, for example from 0 to 10 vol % water.

Whilst syntheses of manganese catalyst salts involving a non-aqueous complexation method can offer some advantages over using alcohol/water mixtures as taught in the prior art, for example in both yield and purity, alternative advantages may be achieved by a complementary syntheses (also involving steps (i) to (iv), but in which, rather than the complexation mixture containing from 0 to 6 wt % of water, it contains more than 6 wt % of water, for example more than 6.001 or more than 6.501 wt % water). For example, such complexation methods can be carried out in pure water, i.e. without a co-solvent, e.g. an organic co-solvent. The pure water can, for example, be demineralised water, sometimes referred to herein as demi-water. Such methods are herein referred to as comprising "an aqueous complexation method"). The use of such aqueous mixtures can be advantageous, for example in reducing emissions of volatile organic chemicals and avoiding the possibility of combustion during spray-drying, for example.

After a synthetic procedure as described above, comprising an aqueous complexation step, the resultant solution after completion of step (iv) typically comprises more than 20% water, for example from 20.001 or 25.501 to 90% vol % water.

Alternatively, after completion of step (iv), where either the non-aqueous or aqueous complexation methods are used, the complex may be comprised in a suspension, slurry or emulsion (rather than a solution).

In the discussion below, reference is made to steps (i) to (iv) with regard to syntheses of manganese catalyst salts involving both (both, unless the context dictates to the contrary) or one of the non-aqueous and aqueous complexation methods.

The rate of formation of the transition metal catalyst as described in steps (i), (ii) and (iii) above depends upon the ligand. The formation of a transition metal catalyst from Me$_3$-TACN ligand is typically complete within 5 minutes. Preferably the complexation mixture is left, optionally under stirring, for at least 20 minutes at a temperature in the range from 20° C. to 80° C. before step (ii) is undertaken. The formation of a transition metal catalyst from Me$_4$-DTNE ligand requires about 20 to 30 minutes for optimal complexation. After complex formation H$_2$O$_2$/base may be slowly added to form, e.g., a desired Mn(IV)/Mn(IV) or Mn(IV)/Mn(III) species (steps (ii), (iii) and (iv)). This second step, the oxidation step, provides a sufficiently stable complex for storage as solid material.

The first step of the non-aqueous complexation method entails dissolution of the ligand in an non-aqueous solvent, after which the manganese salt is added. Suitable and preferred solvents include, but are not limited to, methanol, ethanol, acetonitrile, toluene, acetone, dimethylsulfoxide, dimethylformamide, dichloromethane, tetrahydrofuran, dioxane, ethylene glycol, propylene glycol, 1-propanol, 2-propanol, 1-butanol, 2-butanol, and iso-butanol. OH-containing solvents are preferred, such as methanol, ethanol, 1-propanol, 2-propanol, 1-butanol, 2-butanol, iso-butanol, ethylene glycol, 1,3-propylene glycol, and 1,2-propylene glycol.

Wherein the synthesis involves the aqueous complexation method, also other solvents besides water may be present in the complexation mixture. Suitable and preferred solvents include the same solvents referred to above in connection with the non-aqueous complexation method. Most preferably methanol, ethanol, 1-propanol or 2-propanol are used as co-solvent, if an organic co-solvent is used at all according to the aqueous complexation method.

Manganese salts to be employed for the complexation steps are typically selected from manganese (II) and (III) salts, for example manganese (II) chloride, manganese (II) sulfate, manganese (II) acetate, manganese (III) acetate and manganese (II) nitrate.

When Me$_4$-DTNE type complexes are synthesised and the starting material is not manganese (II) acetate or manganese (III) acetate, additionally carboxylic acid or an alkali salt thereof is generally added in a slight excess of molar equivalent to the ligand. Typically the alkali carboxylate is selected from sodium acetate, potassium acetate, sodium formate, potassium formate, sodium benzoate, sodium propionate and the carboxylic acid is selected from acetic acid, formic acid, benzoic acid, and propionic acid. Most typical are sodium acetate and acetic acid.

In the subsequent step hydrogen peroxide, or a source thereof, is added. Different sources of hydrogen peroxide can be used, such as aqueous hydrogen peroxide, from 3 to 70%, alkali peroxide, urea-hydrogen peroxide, sodium perborate and sodium percarbonate.

It should be noted that introduction of water upon addition of aqueous hydrogen peroxide is essentially unavoidable. However, using concentrated hydrogen peroxide (more than 30%), will result in a level of water that is less than 10 volume %. For this reason, where a non-aqueous complexation method is used, the most preferred range of hydrogen peroxide is from 20 to 55% but hydrogen peroxide is aqueous hydrogen peroxide of from 3 and 70 wt % is acceptable.

Where the aqueous complexation method is used, the hydrogen peroxide, or a source thereof, is typically introduced as an aqueous solution, typically aqueous hydrogen peroxide.

The optimal amount of peroxide is in molar equivalence to the manganese ion, but applying a slight excess to this amount (for example up to 3-fold excess) will not cause major reduction in yields.

Also, additional base is typically added to allow hydrogen peroxide to oxidise the manganese ions. The molar amount of base is approximately similar to the molar amount of peroxide added. NaOH, KOH, and other alkali hydroxides can be employed, with NaOH and KOH being most preferred. Aqueous solutions can be employed (e.g. 5 M solutions) to be added dropwise to the reaction mixtures. Alternatively, particularly where the non-aqueous complexation method has been used, solutions of e.g. KOH in ethanol can be used, to lower the amount of water being present in the reaction medium. Furthermore, sodium or potassium can be added to the neat alcohol solutions, generating the alkali salts of alcohols, which may then be slowly added to the reaction medium.

Before neutralising the alkaline solution, one may optionally filter off the solution containing the manganese complex, in order to remove various impurities, such as non-complexed manganese oxide salts.

After the alkaline oxidation process and optional filtration step (described immediately above), acid is added to obtain a neutral solution (having a pH of about 4 to about 9). Although any organic or inorganic acid may be used, the same acid will generally be used as the salt of the intended complex. For example, therefore, hydrochloric acid is typically used when preparation of the chloride salt is desired. After having neutralised the solution containing the manganese catalyst, this may be optionally filtered in order to remove solid impurities.

Where the preparation of a complex having larger non-coordinating counter ions is desired, such complexes typically being substantially water-insoluble, an additional counterion salt or acid may be added to generate such complexes. These compounds are typically selected from benzoate salts, benzoic acid, NaPF$_6$, KPF$_6$, HPF$_6$, and NaClO$_4$, with sodium benzoate and KPF$_6$ being preferred.

According to the synthetic procedures described above, and others, mixtures comprising manganese transition metal catalysts described herein may be prepared.

According to some embodiments of the first aspect of the invention, the mixture comprising the manganese transition metal catalyst, if spray-dried, may further comprise an inert salt. A variety of salts can be used, for example citrate, chloride, phosphate, sulfate, or acetate salts of sodium, potassium, calcium or magnesium. Typically NaCl is used. The inert salt may, for example, be added to the mixture resultant from step (iv) of the synthetic method described above. The inert salt may be present in any desired concentration in the mixture. Typically, an amount of the inert salt is selected so as to provide a concentration of between about 5 and about 95 wt %, typically between about 25 and about 75 wt %, in the resultant spray-dried powder, e.g. powder according to the second aspect of the invention.

The introduction of an inert salt into a mixture to be spray-dried is advantageous because dilution of the transition-metal complex with such an inert inorganic salt will reduce the likelihood of combustions or explosions occurring during spray-drying.

According to the first aspect of the invention, a liquid mixture, e.g. a solution, suspension, slurry or emulsion (typically a solution) containing the manganese transition metal catalyst, is spray-dried or freeze-dried whereby to provide a powder. This procedure is particularly advantageous if non-coordinating counterions are employed that generate metal complexes having a very high solubility in water, for example more than 30 g/l at 20° C. Such complexes are often hygroscopic and cannot be easily treated at high temperature to evaporate off the water without decomposing at least part of the complex. Therefore, spray-drying or freeze-drying procedures, which allow a fast processing of the catalyst solution, slurry, suspension, or emulsion, are of great benefit.

A typical spray-drying process comprises atomisation of the liquid mixture; drying of the droplets; and separation and recovery of the dried product, typically in powdered form. The solution can be atomised employing, e.g., a pressure nozzle atomiser, which affords very small droplets with a large surface area, and therefore permits a dramatic reduction in drying times and/or temperatures. The inlet temperature is typically between about 70 and about 150° C., and the outlet temperature is typically between 20 and 90° C.

According to some embodiments, therefore, spray-drying comprises
(a) dispersing the mixture, typically an aqueous mixture, of the transition metal catalyst, for example a solution, suspension, slurry or emulsion comprising in the form of drops into a spraying tower; and
(b) supplying a hot gas at a temperature between about 70 and about 150° C. into the spraying tower, and having an outlet temperature comprised between about 20 and about 90° C.,
whereby to provide the spray-dried powder.

Examples of detailed descriptions of spray-drying methods and principles may be found, for example, in Masters, *Spray Drying in Practice*, SprayDryConsult International ApS; Charlottenlund (2002), and www.niro.com (2011). The skilled person may thus readily establish a spray-drying process suitable for practice of an embodiment of the first aspect of the invention.

After spray-drying, the resultant solid, typically in the form of powder, will contain the manganese ion-containing catalyst, the inert salt (if added), water and some minor impurities. It is preferred that the solid contains between 5 and 95 wt %, typically between 25 and 75 wt %, of the inert salt.

As an alternative to spray-drying, the mixture comprising the catalyst may be freeze-dried. Freeze-drying (lyophilization) may be carried out by freezing a mixture, e.g. solution, of the manganese catalyst at a low temperature so as to freeze the mixture of the manganese catalyst and reducing the pressure as required to remove the liquid/solvent from the frozen mixture of the manganese catalyst. The temperature required freeze the mixture will depend on the solvent/liquid present, but will typically range from about −80° C. to about 40° C., Temperatures that may be required to remove the solvent from the frozen mixture may for example be less than about 20° C., or less than about 0° C., or less than about −20° C., or less than about −40° C., or less than about −60° C., or in some cases less than −80° C.

The solid resultant from spray-drying or freeze-drying contains less than 14 wt % water, typically less than 12 wt % water. For example, typical water contents of the dried products are between about 2 and about 12 wt %.

Advantageously, the solid, typically powdered, material resultant from spray-drying or freeze-drying may be further dried to reduce further the amount of water present in the solid product. If conducted, such an additional drying step is more facile (i.e. may be carried out under mild conditions, and causing minimal decomposition of the manganese catalyst), since the majority of the water present in the mixture will have been removed by the spray- or freeze-drying. A combination of drying steps, e.g. a first spray-drying step and then another drying step (which may be a freeze-drying step), may be advantageous in increasing the overall efficiency of the process: through the use of less energy and/or causing less decomposition of the catalyst). A skilled person in the art will be readily able to establish a suitable drying regimen. It is to be understood that effecting additional drying in this way, although not necessary, will generally further improve the storage stability of the catalyst.

Additional drying methods may be selected from one or more of: evaporation under reduced pressure, evaporation of water using a desiccant, such as phosphorus pentoxide ($P_2O_5$), thin-film drying or freeze-drying. Where additional drying comprises or consists of evaporation under reduced pressure typical pressures are less than or equal to about 200 mbar, for example between about 50 mbar and 150 mbar, e.g. about 100 mbar. Optionally, a solvent, such as, but not limited to, ethanol or methanol, may be added and then evaporated under reduced pressure. Additional water removal will be facilitated in this way.

For example, the freeze-dried or spray-dried product may be subjected to vacuum-drying. For example, vacuum-drying may be conducted over a suitable desiccant (for example phosphorus pentoxide) and/or at an elevated temperature (e.g. from about 20 to about 60° C., e.g. between about 40 and about 50° C.). A spray-dried product may be subject to subsequent freeze-drying, which freeze-drying may be conducted as an alternative or in addition to a vacuum-drying step carried out after spray-drying.

The manganese catalysts described herein are often associated with one or more molar equivalents of water molecules. The presence of such water molecules may be analysed, for example, using X-ray structure analysis. Wieghardt et al. (*J. Am. Chem. Soc.*, 110, 7398 (1988)) showed, for example, that a manganese complex comprising Me$_3$TACN, and PF$_6$ as counterion, has one water molecule in the structure.

Alternatively, extensive drying (e.g. at low temperature under reduced pressure) may be effected so as to remove what is referred to herein as free water (as opposed to hydrating water molecules). The quantity of residual water molecules may then be analysed, for example by Karl Fisher analysis. For [Mn$^{III}$Mn$^{IV}$($\mu$-O)$_2$($\mu$-CH$_3$COO)(Me$_4$-DTNE)]Cl$_2$, it was determined that one water molecule is in the crystal lattice, whilst for [(Mn$^{IV}$)$_2$($\mu$-O)$_3$(Me$_3$-TACN)$_2$]SO$_4$ there are four water molecules present per molecule of catalyst. It should be noted that in the descriptions of catalysts set forth above, no additional lattice water is taken into the structures.

The term hydrate is well known in the art to define inorganic salts containing water molecules combined in a definite ratio as an integral part of the crystal. In the case of the manganese complexes, the water molecules have crystallised with the metal complexes. Often those water molecules are held together to the core complex via strong hydrogen-bonding interactions, e.g. between the complex and water or counterion and water. The manganese complexes may after very careful drying contain only water of hydration, which may be analysed. Prior to such drying, however, free water will be present as well as water of hydration. When drying via spray-drying or freeze-drying, first the non-hydrate (free) water molecules are removed, as these will have much weaker hydrogen-bonding interactions, if any; the hydrate water molecules will remain owing to the stronger hydrogen bonding. From these considerations, the skilled person will understand that the stoichiometry of "hydrating" water molecules for any particular composition may be ascertained by conducting thermogravimetric analysis (TGA) on the composition concerned, since this will allow quantitation of the free water molecules and the hydrate water molecules.

Without wishing to be bound by theory, we believe that it is excess free water that causes destabilisation of the catalysts described herein upon storage. Therefore, careful drying to obtain compositions with only hydrating molecules of water is particularly advantageous. It will be understood that the stoichiometry of hydrating water molecules depend on the identity of any particular compound. For example, where the catalyst is $[(Mn^{IV})_2(\mu-O)_3(Me_3-TACN)_2]SO_4$, and other catalysts which typically form a tetrahydrate, typical weight percentages of water in accordance with the present invention are approximately 10 to 14 wt %; whereas, where the catalyst is $[Mn^{III}Mn^{IV}(\mu-O)_2(\mu-CH_3COO)(Me_4-DTNE)]Cl_2$, and other catalysts which typically form a monohydrate, typical weight percentages of water in accordance with the present invention are approximately 3 to 7 wt %.

According to particular embodiments of both aspects of the invention, including the various embodiments described herein, the concentration of non-hydrating water is less than 7 wt %, for example between about 0.01 and 7 wt %, e.g. between about 0.5 and 7 wt %, such as less than 5 wt %, for example less than 4%.

The complexes prepared according to the first aspect of the invention and according to the second aspect of the invention are typically stable for at least 4 weeks at 30° C. Although not strictly necessary, it is preferred that the complexation step is carried in an oxygen-free atmosphere, for example under nitrogen or argon. Also, it is preferable that the resultant solid materials comprising the catalyst are stored under nitrogen or argon gas, typically nitrogen.

The manganese catalyst produced according to the first aspect of this invention and according to the second aspect of the invention may be used in a bleaching process or cellulose/starch treatment process. In such uses, it is typical for the substrate to be contacted with from 0.001 to 100 micromolar of the transition metal catalyst and from 5 to 1500 mM of hydrogen peroxide. Typically the transition metal catalyst salt and hydrogen peroxide are mixed just before introduction to the substrate.

All publications (patent and non-patent) referred to herein are incorporated by reference in their entireties, as if the entire contents of each reference was set forth herein in its entirety.

The invention may be further understood with regard to the following non-limiting clauses:

1. A method of preparing a powder comprising a manganese transition metal catalyst of a ligand of formula (I):

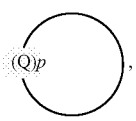

(wherein:

p is 3;
R is independently selected from: hydrogen, C1-C6-alkyl, C2OH, C1COOH, and pyridin-2-ylmethyl or one of R is linked to the N of another Q from another ring via an ethylene bridge; and R1, R2, R3, and R4 are independently selected from: H, C1-C4-alkyl, and C1-C4-alkylhydroxy) and less than 14 wt % of water, the method comprising spray-drying or freeze-drying a mixture comprising the catalyst.

2. The method of clause 1 wherein the powder comprises less than 12 wt % water.

3. The method of clause 1 or clause 2 wherein the spray-drying or freeze-drying is of a mixture that comprises more than 20% water.

4. The method of any one of clauses 1 to 3 wherein the method further comprises a synthesis of the catalyst, prior to the spray-drying or freeze-drying, in which a complexation between manganese ion(s) and the ligand of formula (I) is effected in a complexation mixture comprising more than 6 wt % of water.

5. The method of any one preceding clause, wherein R is independently selected from: $CH_3$, $C_2H_5$, $CH_2CH_2OH$ and $CH_2COOH$.

6. The method of any one preceding clause, wherein R1, R2, R3, and R4 are independently selected from H and Me.

7. The method of any one preceding clause, wherein the ligand is selected from 1,4,7-trimethyl-1,4,7-triazacyclononane ($Me_3$-TACN) and 1,2-bis-(4,7-dimethyl-1,4,7-triazacyclonon-1-yl)-ethane ($Me_4$-DTNE).

8. The method of any one preceding clause, wherein the catalyst is a salt of the metal complexes $[(Mn^{IV})_2(\mu-O)_3(Me_3-TACN)_2]^{2+}$, $[(Mn^{III})_2(\mu-O)(\mu-CH_3COO)_2(Me_3-TACN)_2)]^{2+}$ or $[Mn^{III}Mn^{IV}(\mu-O)_2(\mu-CH_3COO)(Me_4-DTNE)]^{2+}$.

9. The method of any one preceding clause, wherein the manganese catalyst has a non-coordinating counterion selected to provide a preformed transition-metal catalyst that has a water solubility of at least 30 g/l at 20° C.

10. The method of clause 9, wherein the non-coordinating counterion is selected from chloride, bromide, sulfate, nitrate, acetate, and benzoate.

11. The method of any one preceding clause, wherein the catalyst is selected from the group comprising $[(Mn^{IV})_2(\mu-O)_3(Me_3-TACN)_2]SO_4$, $[Mn^{III}Mn^{IV}(\mu-O)_2(\mu-CH_3COO)(Me_4-DTNE)]Cl_2$, $[(Mn^{IV})_2(\mu-O)(Me_3-TACN)_2](CH_3COO)_2$, $[(Mn^{IV})_2(\mu-O)_3(Me_3-TACN)_2](NO_3)_2$ and $[Mn^{III}Mn^{IV}(\mu-O)_2(\mu-CH_3COO)(Me_4-DTNE)](NO_3)_2$.

12. The method of clause 11, wherein the catalyst is $[(Mn^{IV})_2(\mu-O)_3(Me_3-TACN)_2]SO_4$.

13. The method of clause 11, wherein the catalyst is $[Mn^{III}Mn^{IV}(\mu-O)_2(\mu-CH_3COO)(Me_4-DTNE)]Cl_2$.

14. The method of any one preceding clause, wherein the spray-drying or freeze-drying is of an aqueous mixture.

15. The method of any one preceding clause, wherein the spray-drying or freeze-drying is of a solution.

16. The method of any one preceding clause, wherein the powder is further dried under reduced pressure after spray-drying step or freeze-drying, so that the resultant powder comprises less than 10 wt % water.

17. The method clause 16, wherein the resultant powder comprises less than 6 wt % water.

18. The method of any one preceding clause, wherein the mixture is spray-dried and the spray-drying comprises
  (a) dispersing the mixture of the transition metal catalyst comprising in the form of drops into a spraying tower; and
  (b) supplying a hot gas at a temperature between about 70 and about 150° C. into the spraying tower, and having an outlet temperature comprised between about 20 and about 90° C.,
whereby to provide the spray-dried powder.

19. The method of any one preceding clause, wherein the mixture that is spray-dried further comprises an inorganic salt.
20. The method of clause 19, wherein the salt is selected from the group consisting of citrate, chloride, phosphate, sulfate, or acetate salts of sodium, potassium, calcium or magnesium.
21. The method of clause 19, wherein the salt is sodium chloride.
22. A powder comprising a manganese transition metal catalyst as defined in clause 1 and less than 14 wt % of water.
23. The powder of clause 22, which comprises less than 12 wt % water.
24. The powder of clause 22, which comprises less than 10 wt % water.
25. The powder of clause 22, which comprises less than 6 wt % water.
26. The powder of any one of clauses 22 to 25, which comprises between 5 and 95 wt % NaCl.
27. The powder of any of clauses 22 to 26, which comprises between 25 and 75 wt % NaCl.
28. The powder of any one of clauses 22 to 27, wherein the catalyst is as defined in any one of clauses 5 to 11.
29. The powder of clause 28, wherein the catalyst is $[(Mn^{IV})_2(\mu-O)_3(Me_3-TACN)_2]SO_4$.
30. The powder of clause 28, wherein the catalyst is $[Mn^{III}Mn^{IV}(\mu-O)_2(\mu-CH_3COO)(Me_4-DTNE)]Cl_2$.

Each document referred to herein (both patent and non-patent literature) is incorporated herein by reference as if the entire contents of each was recited in its entirety.

The invention is now illustrated by the following non-limiting examples.

Example 1: Preparation of $[(Mn_2(\mu-O)_2(\mu-OAc)(Me_4-DTNE)]Cl_2 \cdot H_2O$ (Ethanol and Water Route) Using Spray-Drying without Addition of Sodium Chloride Under $N_2$, to $Me_4$-DTNE (95% purity, 0.3 mol) in ethanol or demi-water (750 gram), solid mixture of $MnCl_2 \cdot 4H_2O$ (99% purity, 0.66 mol) and sodium acetate (NaOAc) (99% purity, 0.15 mol) were added. The mixture was stirred for 30 min at 58° C. After another stirring for 10 min cooled in an ice water bath, the freshly prepared mixture of 3.5 M of $H_2O_2$ in water (382 gram, 0.68 mol) and 5 M of NaOH (101 g, 0.5 mol) was added drop-wise over 30 min. The mixture turned immediately dark green-brown. The mixture was stirred for 30 min in an ice water bath and then for 40 min at room temperature. Glacial acetic acid (0.2 mol) was added. After stirring for another 30 min, the mixture was filtered to remove brown solid and the filtering bed was washed with water or ethanol. Weight the solution and test pH value and the density. From this green solution, a 100 times dilution and a 4000 times dilution were made; and from the absorption in the UV-Vis spectrum at the wavelengths of 244 nm from 4000 times dilution, 554 nm from 100 times dilution, and 639 nm from 100 times dilution, the concentration in the stock and the conversion were calculated, based on the molar extinction coefficient of $[Mn_2(\mu-O)_2(\mu-OAc)(Me_4-DTNE)]Cl_2$ with Mw 612 in water for 100% pure, ε $(mol^{-1} \cdot L \cdot cm^{-1})$: 271 nm (13200 $mol^{-1} \cdot L \cdot cm^{-1}$), 554 nm (315 $mol^{-1} \cdot L \cdot cm^{-1}$), 639 nm (325 $mol^{-1} \cdot L \cdot cm^{-1}$).

1.1 Ethanol Route

The weight of the green filtrate was 1842 g, and pH value was 7.02, and the density was 1.06 g/mL. The conversion was around 100%. The concentration was 10%.

895 gram of the green solution was used in spray-drying. Under the conditions of 90-110° C. of the inlet temperature, 45-55° C. of the outlet temperature, 1.8 kg per hour of liquid velocity, the spray-drying with rotary spray type was done within 2 hours. The spray-drying equipment was a Wuxi Yang Guan type LPG-5.

The green powder was collected (71 g, 74% purity, 8.8% water) and dried overnight at 45° C. over $P_2O_5$ in vacuum to afford dark green powder with the particle size of 5-25 μm as $[(Mn_2(\mu-O)_2(\mu-OAc)(Me_4-DTNE)]Cl_2 \cdot H_2O$ with 66.8 gram and 79% UV-Vis purity, 3% water, 59% yield.

1.2 Water Route

The weight of the green filtrate was 1553 g, and pH value was 6.94, and the density was 1.06 g/mL. The conversion was around 100%. The concentration was 11.6%.

Under the conditions of 120-130° C. of the inlet temperature, 45-55° C. of the outlet temperature, 1.8 kg per hour of liquid velocity, the spray-drying with rotary spray type was done within 2 hours. The spray-drying equipment was a Wuxi Yang Guan type LPG-5. The green powder was collected and dried overnight at 45° C. over $P_2O_5$ in vacuum to afford dark green powder with the particle size of 5-25 μm as $[(Mn_2(\mu-O)_2(\mu-OAc)(Me_4-DTNE)]Cl_2 \cdot H_2O$ with 162 gram and 71% UV-Vis purity, 2.5% water, 66% yield.

1.3 Solid Stability Test

The samples obtained as described in example 7.1 with 3% water and example 7.2 contained 2.5% water, were subjected to a storage test (close vessel at 50° C. for 4 weeks under nitrogen). For both samples, less than 5% of the compound was then decomposed, showing that the compound spray-dried, followed by drying in vacuo exhibits excellent storage stability.

Example 2: Preparation of $[(Mn_2(\mu-O)_2(\mu-OAc)(Me_4-DTNE)]Cl_2 \cdot H_2O$ (Using Aqueous Complexation Method) and Spray-Drying with Addition of Extra Sodium Chloride Under $N_2$, to $Me_4$-DTNE (95% purity, 8 mol) in demi-water (10 kilogram), solid mixture of $MnCl_2 \cdot 4H_2O$ (99% purity, 17.6 mol) and NaAc (99% purity, 4 mol) were added. The mixture was stirred for 30 min at 58° C. After another stirring for 10 min cooled in an ice water bath, the freshly prepared mixture of 3.5 M of $H_2O_2$ in water (18 mol) and 5 M of NaOH (13.5 mol) was added drop-wise over 60 min. The mixture turned immediately dark green-brown. The mixture was stirred for 30 min in an ice water bath and then for 40 min at room temperature. Glacial acetic acid (5 mmol) was added. After stirring for another 30 min, the mixture was filtered to remove brown solid and the filtering bed was washed with water. The weight of the green filtrate was 27.1 kg, and pH value was 7.20, and the density was 1.06 g/mL. From this green solution, a 100 times dilution and a 4000 times dilution were made; and from the absorption in the UV-Vis spectrum at the wavelengths of 244 nm from 4000 times dilution, 554 nm from 100 times dilution, and 639 nm from 100 times dilution, the concentration in the stock and the conversion were calculated, based on the molar extinction coefficient of $[Mn_2(\mu-O)_2(\mu-OAc)(Me_4-DTNE)]Cl_2$ with Mw 612 in water for 100% pure, ε $(mol^{-1} \cdot L \cdot cm^{-1})$: 271 nm (13200 $mol^{-1} \cdot L \cdot cm^{-1}$), 554 nm (315 $mol^{-1} \cdot L \cdot cm^{-1}$), 639 nm (325 $mol^{-1} \cdot L \cdot cm^{-1}$).

271 nm 0.921
554 nm 0.896
639 nm 0.906

The conversion was around 100%. The concentration was 18%.

1.05 kilogram of NaCl was added to 16.25 kg of the green solution with the stirring for 40 min at room temperature. Under the conditions of 120-160° C. of the inlet temperature, 60-100° C. of the outlet temperature, 20 kg per hour of liquid velocity, the spray-drying with rotary spray type was done within 2 hours. The spray-drying equipment was a Wuxi Yang Guan type LPG-20. Collect the green powder and dry overnight at 45° C. over $P_2O_5$ in vacuum to afford dark green powder with the particle size of 5-25 µm as [$(Mn_2(\mu-O)_2(\mu-OAc)(Me_4-DTNE)]Cl_2.H_2O$ with 6.3 kilogram and 50% UV-Vis purity and 4% water content, 68% yield.

The compound with 50% UV-Vis purity and around 46% of sodium chloride was stored at 4° C., 30° C., and 50° C. over 8 weeks, respectively. The compound lost below 5% at 4° C. and 30° C. over 8 weeks and 10-20% at 50° C. over 8 weeks.

Example 3: Preparation of [$(Mn_2(\mu-O)_2(\mu-OAc)(Me_4-DTNE)]Cl_2.H_2O$ (Ethanol/Water Complexation Route) from Freeze-Drying Under $N_2$, to $Me_4$-DTNE (95% purity, 2.85 mol) in ethanol (21.4 kg) and demi-water (10.7 kg), solid mixture of $MnCl_2.4H_2O$ (99% purity, 6.27 mol) and NaAc (99% purity, 1.425 mol) were added. The mixture was stirred for 30 min at 58° C. After another stirring for 10 min cooled in an ice water bath, the freshly prepared mixture of 1 M of $H_2O_2$ in water (6.41 mol) and 1.5 M of NaOH (4.81 mol) was added drop-wise over 60 min. The mixture turned immediately dark green-brown. The mixture was stirred for 30 min in an ice water bath and then for 40 min at room temperature. 1M of acetic acid (1.78 mmol) was added. After stirring for another 30 min, the mixture was filtered to remove brown solid and the filtering bed was washed with ethanol. Then the green filtrate was evaporated (the water bath temperature <45° C.). The residual dark green oil was co-evaporated with ethanol and ethyl acetate to facilitate the removal of most of the remaining water. Dark green oils were taken up in ethanol, and the insoluble white salts separated by filtration were washed with ethanol. After removing all ethanol by evaporation in vacuo, the dark green oil was obtained again. The small amount of ethanol was added and stirred for 10 min. Then the large amount of ethyl acetate was added. The green solid was precipitated immediately. After 3 hours at −20° C., the suspension was filtered off, with obtaining a green solid, which was washed with ethyl acetate, n-hexane, and dried under vacuum at 45° C. for 5 hrs to afford dark green powder as [$(Mn_2(\mu-O)_2(\mu-OAc)(Me_4-DTNE)]Cl_2.H_2O$, 1.15 kg, with 86.4% UV-Vis purity and 54% yield.

Then 1.15 kg of the above-mentioned sample was dissolved in 22 kg of demineralised water, which was left at room temperature for 2 hours and was then filtered off to remove some brown precipitate. The filtrate was put in the freeze plate of the freeze-drying machine with the 2 cm depth. The freeze-drying equipment used was a Shanghai Dong Fu Long type LYO-10. The water in the filtrate was removed by freeze-drying process for 36 hours in vacuum around 100-500 Pascal. The freeze-drying equipment was a Shanghai Dong Fu Long type LYO-10. The green powder was collected as [$(Mn_2(\mu-O)_2(\mu-OAc)(Me_4-DTNE)]Cl_2.H_2O$ (1.01 kilogram) with a 81% UV-Vis purity, 88% yield of freeze-drying.

Analyses

UV-Vis spectrum ($\varepsilon$: $mol^{-1} \cdot L \cdot cm^{-1}$, in water): 271 nm (10219), 554 nm (241), 639 nm (260).

UPLC analysis confirmed 1.8% of free [$H_2(Me_4-DTNE)$]$Cl_2$.

Total chloride amount was 12.2%.
Water analysis by Karl-Fischer method: 1.81%.
Ash analysis: 22.6%.

By using the extraction process with water and subsequently freeze-drying process, the amount of impurity of ($H_2Me_4$-DTNE)$Cl_2$ has been greatly reduced from 6.9% to 1.8%. After freeze-drying, the residual water content was very low (less than 2%).

Although not carried out in this experiment, the freeze-drying process could be used immediately after the synthesis of the manganese catalyst complex in water. When getting compound's aqueous solution via water route, the water can be removed directly by the freeze-drying process. This would not take any risk of the degradation of the compound without the condition of heating, when carrying out a heat-induced evaporation procedure.

Example 4: Preparation of [$(Mn_2(\mu-O)_3(Me_3-TACN)_2](CH_3COO)_2.4H_2O$ from Spray-Drying Process Under $N_2$, the mixture of $Me_3$-TACN (95% purity, 0.38 mol), manganese(II) acetate (0.4 mol) in 450 g of demi-water was stirred for 20 min at room temperature. After another stirring for 10 min cooled in an ice water bath, a freshly prepared mixture of 3.5% $H_2O_2$ (0.485 mol) and 20% NaOH (0.575 mol) was added dropwise over 5-10 min. The mixture turned immediately dark brown/red. The mixture was further stirred for 20 min in an ice bath and for another 40 min at room temperature. Glacial acetic acid (0.4 mol) was added and stirred for 30 min in order to adjust pH value to 5. The red-wine mixture was filtered to remove brown solid and the filtering bed was washed with water. Weight the solution and test pH value and the density.

From this green solution, a 1000 times dilution were made; and from the absorption in the UV-Vis spectrum at the wavelengths of 244 nm, 278 nm, and 313 nm, the concentration in the stock and the conversion were calculated, based on the molar extinction coefficient of [$(Mn_2(\mu-O)_3(Me_3-TACN)_2](PF_6)_2.H_2O$ in water for 100% pure, $\varepsilon$ ($mol^{-1} \cdot L \cdot cm^{-1}$): 244 nm (19300 $mol^{-1} \cdot L \cdot cm^{-1}$), 278 nm (18600 $mol^{-1} \cdot L \cdot cm^{-1}$), 313 nm (12000 $mol^{-1} \cdot L \cdot cm^{-1}$), 389 nm (1100 $mol^{-1} \cdot L \cdot cm^{-1}$), 485 nm (465 $mol^{-1} \cdot L \cdot cm^{-1}$).

244 nm 2.284
278 nm 2.186
313 nm 1.415

The weight of the green filtrate was 1434 g, and pH value was 5.33, and the density was 1.04 g/mL. The conversion was 87.5%. The concentration was 7.13%.

Under the conditions of 100-130° C. of the inlet temperature, 40-55° C. of the outlet temperature, 1.8 kg per hour of liquid velocity, the spray-drying with rotary spray type was done within 2 hours. The spray-drying equipment was a Wuxi Yang Guan type LPG-5. Collect the red powder and dry overnight at 45° C. over $P_2O_5$ in vacuum to afford red powder with the particle size of 5-25 µm as [$(Mn_2(\mu-O)_3(Me_3-TACN)_2](CH_3COO)_2.4H_2O$ with 62 gram and 59.3% UV-Vis purity, 30% yield.

UV-Vis spectrum ($\varepsilon$: $mol^{-1} \cdot L \cdot cm^{-1}$, in water, Mw 690): 244 nm (11581), 278 nm (10980), 313 nm (7073), 389 nm (696), 485 nm (287).

Example 5: Preparation of [$(Mn_2(\mu-O)_3(Me_3-TACN)_2]SO_4.4H_2O$ from Spray-Drying Process Under $N_2$, the mixture of $Me_3$-TACN (97% purity, 200 mmol), manganese(II)sulphate (220 mmol) in 300 g of demi-water was stirred for 20 min at room temperature. After another stirring for 10 min cooled in an ice water bath, a freshly prepared mixture of 3.5% $H_2O_2$ (240 mmol) and 6% NaOH (300 mmol) was added dropwise over 5-10 min. The mixture turned immediately dark brown/red. The mixture was further stirred for 20 min in an ice bath and for another 40 min at room temperature. 1 M $H_2SO_4$ (40 mmol) was added and stirred for 30 min in order to adjust pH value to 5. The red-wine mixture was filtered to remove brown solid and the filtering bed was washed with water.

Weight the solution and test pH value and the density. From this green solution, a 1000 times dilution were made; and from the absorption in the UV-Vis spectrum at the wavelengths of 244 nm, 278 nm, and 313 nm, the concentration in the stock and the conversion were calculated, based on the molar extinction coefficient of $[Mn_2(\mu-O)_3(Me_3\text{-}TACN)_2](PF_6)_2 \cdot H_2O$ in water for 100% pure, $\varepsilon$ ($mol^{-1} \cdot L \cdot cm^{-1}$): 244 nm (19300 $mol^{-1} \cdot L \cdot cm^{-1}$), 278 nm (18600 $mol^{-1} \cdot L \cdot cm^{-1}$), 313 nm (12000 $mol^{-1} \cdot L \cdot cm^{-1}$), 389 nm (1100 $mol^{-1} \cdot L \cdot cm^{-1}$), 485 nm (465 $mol^{-1} \cdot L \cdot cm^{-1}$).

The weight of the green filtrate was 918 g, and pH value was 5, and the density was 1.04 g/mL. The conversion was 96.4%. The concentration was 6.4%.

Under the conditions of 110-160° C. of the inlet temperature, 40-100° C. of the outlet temperature, 20 kg per hour of liquid velocity, the spray-drying with rotary spray type was done within 2 hours. Collect the red powder with 74% UV-Vis purity and 18% water and dry overnight at 45° C. over $P_2O_5$ in vacuum to afford red powder with the particle size of 5-25 μm as $[(Mn_2(\mu-O)_3(Me_3\text{-}TACN)_2]SO_4 \cdot 4H_2O$ with 30 gram and 79% UV-Vis purity and 12% water, 35% yield.

Analyses after Drying Over $P_2O_5$.

UV-Vis spectrum ($\varepsilon$: $mol^{-1} \cdot L \cdot cm^{-1}$, in water, Mw 668): 244 nm (15338), 278 nm (14627), 313 nm (9449), 389 nm (899), 485 nm (384).

UPLC analysis confirmed the trace amounts of free $[H_2(Me_3\text{-}TACN)]SO_4$ and $Me_5\text{-}Dien$.

Total sulphate amount was 22%, so, the content of free sodium sulphate was 16%.

Ash analysis: 47.56%.

Water analysis by Karl-Fischer method: 12%.

IR (KBr pellet): 3461br, 3363br, 3020w, 2929w, 1642w, 1506w, 1454m, 1420w, 1295w, 1120vs, 1052s, 1005s, 981m, 902w, 791m, 747w, 696w, 660m, 618m, 561m $cm^{-1}$.

$^1$H-NMR ($D_2O$, 400 MHz) (δ, ppm): 2.20 (br, 42H, $NCH_3+NCH_2$). No more residual impurities peak.

Example 6: Preparation of $[(Mn_2(\mu-O)_3(Me_3\text{-}TACN)_2]SO_4 \cdot 4H_2O$ with Different Levels of Water (No Spray-Drying Process)

Under $N_2$, the mixture of $Me_3$-TACN (99% purity, 10 mmol), manganese(II) sulphate (11 mmol), in demi-water (30 mL) was stirred for 20 min at room temperature. After another stirring for 10 min cooled in an ice water bath, a freshly prepared mixture of 1 M $H_2O_2$ (12.5 mmol) and 1.5 M NaOH (15 mmol) was added dropwise over 5-10 min. The mixture turned immediately dark brown/red. The mixture was further stirred for 20 min in an ice bath and for another 40 min at room temperature. 1M $H_2SO_4$ (3.3 mmol) was added and stirred for 30 min in order to adjust pH value to 5. The red-wine mixture was filtered to remove brown solid and the filtering bed was washed with ethanol. The filtrate was reduced in vacuo (water bath: 35° C.-40° C.) to afford a red-oil. The residue was dissolved in ethanol, and the insoluble white salts separated by filtration were washed with ethanol. The ethanol filtrate combined was evaporated to dryness obtaining a red-oil. The red-oil was washed with acetonitrile and ethyl acetate until obtaining red solid, which was dried in vacuum over $P_2O_5$ at 45° C. for 6 hrs to afford red solid as $[(Mn_2(\mu-O)_3(Me_3\text{-}TACN)_2]SO_4 \cdot 4H_2O$.

Sample A

Red solid, 91% yield, >95% purity.

Anal. calcd. for $C_{18}H_{50}Mn_2N_6O_{11}S$: C, 32.34; H, 7.54; N, 12.57. Found: C, 32.54; H, 7.74; N, 12.57%.

IR (KBr pellet): 3453br, 2923w, 1646m, 1532m, 1460m, 1120vs, 1056m, 1005m, 792m, 747w, 664m, 621m, 563m $cm^{-1}$.

$^1$H-NMR ($D_2O$, 400 MHz) (δ: ppm): 2.25 (br, 42H, $NCH_3+NCH_2$).

UV-Vis spectrum ($\varepsilon$: $mol^{-1} \cdot L \cdot cm^{-1}$, in water): 244 nm (19669), 280 nm (18424), 315 nm (11787), 394 nm (1151), 485 nm (488).

Water analysis (Karl-Fischer method): 9.86%.

Free $(HMe_3Tacn)_2SO_4$ (UPLC): 1.80% (wt %).

Free $Me_5$-DIEN analysis (UPLC): 0.12% (wt %).

MS-ES$^+$: m/e 250.1.

HPLC-UV/Vis: 8.17 min (245, 280, 316, 390, 482 nm).

HPLC-MS/ES$^+$: 8.40 min (m/e: 250 (100%), 235 (48%)).

Sample B

The similar preparation to Sample A, except that the scale was done on large scale. Now 400 gram of red solid as $[(Mn_2(\mu-O)_3(Me_3\text{-}TACN)_2]SO_4 \cdot 4H_2O$ was isolated.

Red solid, 87% purity.

IR (KBr pellet): 3409 br, 2927m, 1640m, 1454s, 1294m, 1121vs, 1052m, 1004m, 902w, 791m, 747m, 665m, 619m, 562m $cm^{-1}$.

UV-Vis ($\varepsilon$: $mol^{-1} \cdot L \cdot cm^{-1}$, in water): 244 nm (17014), 278 nm (16180), 313 nm (10409), 389 nm (948), 485 nm (376).

Water analysis (Karl-Fischer method): 16.5%.

$^1$H NMR ($D_2O$, 400 MHz) (δ: ppm): 2.25 (br, 42H, $NCH_3+NCH_2$).

Free ($H_2Me_3Tacn$) $SO_4$ (UPLC): 1.80% (wt %).

Free $Me_5Dien$ (UPLC): below 0.06% (wt %).

HPLC-MS/ES$^+$: 12.20 min (m/e: 250 (100%), 235 (25%)).

HPLC-UV/Vis: 11.97 min (280, 316, 390, 482 nm).

Sample C 5.4 gram of Sample B was taken and dried at 50° C. for 4 hours in vacuum over $P_2O_5$.

Red solid, 93% purity.

Water analysis (Karl-Fischer method): 10%.

Free $(HMe_3Tacn)_2SO_4$ (UPLC): 0.96% (wt %).

Free $Me_5Dien$ (UPLC): below 0.10% (wt %).

Storage Stability Tests

The amount of water in the compound had a great effect on the solid stability. Sample A was a good quality sample with 9.86% water. Sample B was a poor quality sample with 16.5% water. Sample C with 10% water was obtained from the re-dryness of Sample B. The three samples were stored at 50° C. for 2 weeks and purity tested by UV-vis. The lost amounts (in %) was calculation, as shown in Table 1. Lost percentage was given from the below formula.

$$\text{Lost percentage (\%)} = (P_{before\ stability} - P_{after\ stability})/P_{before\ stability} \times 100\%$$

Where: $P_{before\ stability}$ was the purity (%) obtained from the absorption value of UV-Vis spectrum at the beginning of the stability test and $P_{after\ stability}$ was the purity (%) obtained from the absorption value of UV-Vis spectrum after doing stability test at the $1^{st}$ week and the $2^{nd}$ week.

TABLE 1

| Sample | UV-Vis purity (%) | The amount of water (%) | Lost percentage (%) | |
|---|---|---|---|---|
| | | | 1 week | 2 weeks |
| Sample A | >95 | 9.86 | 6.7 | 6.6 |
| Sample B | 87 | 16.5 | 69.0 | 89.1 |
| Sample C | 93 | 10 | 2.2 | 3.0 |

Visually, it was noted that Sample B has changed the colour from red to brown after 2 weeks storage, which indicates a complete degradation of the compound. The same sample that has been dried before storing (sample C) did show a good storage stability (similar to that of sample A), both based on UV-vis analyses and on visual assessment. Therefore it is concluded that obtaining the compound in a dry state (<10%) improves storage stability and handling considerably.

Examples 7 to 13 below describe preparation of various catalysts as described herein and which are subjected to vacuum-drying rather than spray-drying or freeze-drying. The skilled person will be readily able to adapt the drying step described in these examples for a spray-drying or freeze-drying step. The examples are thus useful for further understanding the invention rather than being examples of it.

Example 7: Preparation of [$Mn_2(\mu-O)_2(\mu-CH_3COO)$(Me$_4$-DTNE)]Cl2 According to Methods Known in the Prior Art Under $N_2$, to Me$_4$-DTNE (95% purity, 4 mmol) in different solvents (40 mL), solid mixture of $MnCl_2 \cdot 4H_2O$ (99% purity, 8.8 mmol) and sodium acetate (99% purity, 2 mmol) were added. The mixture was stirred for 30 min at 58° C. After another stirring for 10 min cooled in an ice water bath, the freshly prepared mixture of 1 M of $H_2O_2$ in water (9 mL, 9 mmol) and 1.5 M of NaOH (4.5 mL, 6.75 mmol) was added drop-wise over 5 min. The mixture turned immediately dark green-brown. The mixture was stirred for 20 min in an ice water bath and then for 20 min at room temperature. 1 M of acetic acid (2.5 mmol) was added. After stirring for another 20 min, the mixture was filtered to remove brown solid and the filtering bed was washed with ethanol. Then the green filtrate was evaporated (the water bath temperature <45° C.). The residual dark green oil was co-evaporated with ethanol and ethyl acetate to facilitate the removal of most of the remaining water. Dark green oils were taken up in ethanol (20 mL), and the insoluble white salts separated by filtration were washed with ethanol. After removing all ethanol, the dark green oil was obtained again. The small amount of ethanol was added and stirred for 2 min. Then the large amount of ethyl acetate was added. The green solid was precipitated immediately. After 3 hours at −20° C., the suspension was filtered off, with obtaining a green solid, which was washed with ethyl acetate, n-hexane, and dried under vacuum at 45° C. for 5 hrs to afford dark green powder as [($Mn_2(\mu-O)_2(\mu-OAc)(Me_4$-DTNE)]$Cl_2 \cdot H_2O$.

7.1 EtOH/$H_2O$ (2:1, v/v) Benchmark

Ethanol/water (2:1, v/v): 40 mL; yielding a green powder, UV-Vis purity of 85.3%, and the yield of 88%.

UV-Vis spectrum ($\epsilon$: $mol^{-1} \cdot L \cdot cm^{-1}$, in water, Mw: 630): 271 nm (11794), 554 nm (258), 639 nm (275).

IR (KBr pellet): 3421 br, 2921w, 1604m, 1568w, 1499w, 1463s, 1395s, 1337w, 1286w, 1159w, 1076w, 1057w, 1032w, 1004w, 985w, 912w, 779w, 744w, 678m, 614m cm$^{-1}$.

UPLC analysis confirmed the 12.45% of free [$H_2(Me_4$-DTNE)]$Cl_2$.

Total chloride amount was 13.10%.

Water analysis (Karl-Fischer method): Anal. calcd. for [($Mn_2(\mu-O)_2(\mu-OAc)(Me_4$-DTNE)]$Cl_2 \cdot H_2O$: 2.86%. Found: 4.10%.

7.2 $H_2O$, Benchmark

Demineralised water: 40 mL; yielding a green powder, UV-Vis purity of 63.8%, and the yield of 54%.

UV-Vis spectrum ($\epsilon$: $mol^{-1} \cdot L \cdot cm^{-1}$, in water, Mw: 630): 271 nm (8100), 554 nm (209), 639 nm (208).

IR (KBr pellet): 3425 br, 2921m, 1604m, 1567m, 1497w, 1463s, 1394s, 1338m, 1293w, 1159w, 1076w, 1057w, 1032w, 1004m, 985w, 912w, 779w, 744w, 678m, 613m cm$^{-1}$. UPLC analysis confirmed the amount of free [$H_2(Me_4$-DTNE)]$Cl_2$ was 6.79%.

Total chloride amount was 12.22%.

Water analysis (Karl-Fischer method): Anal. calcd. for [($Mn_2(\mu-O)_2(\mu-OAc)(Me_4$-DTNE)]$Cl_2 \cdot H_2O$: 2.86%. Found: 4.30%.

Example 8: Preparation of Solid [$Mn_2(\mu-O)_2(\mu-CH_3COO)(Me_4$-DTNE)]$Cl_2$ Using Non-Aqueous Solvents for Complexation Under $N_2$, to Me$_4$-DTNE (95% purity, 4 mmol) in different solvents (10 mL to 40 mL), solid mixture of $MnCl_2$ (99% purity, 8.8 mmol) and sodium acetate (99% purity, 2 mmol) were added. The mixture was stirred for 30 min at 58° C. (as for $CH_2Cl_2$, 40° C. for 30 min). After another stirring for 10 min cooled in an ice water bath, the freshly prepared mixture of 1 M of $H_2O_2$ in water (9 mL, 9 mmol) and 5 M of NaOH (1.35 mL, 6.75 mmol) was added drop-wise over 5 min. The mixture turned immediately dark green-brown. The mixture was stirred for 20 min in an ice water bath and then for 20 min at room temperature. Glacial acetic acid (2.5 mmol) was added. After stirring for another 20 min, the mixture was filtered to remove brown solid and the filtering bed was washed with ethanol. In each case, the solvent in the green solution were evaporated (the water bath temperature <45° C.), with obtaining dark green oil, which were taken up in ethanol (20 mL). The insoluble white salts separated by filtration were washed with ethanol. After removing all ethanol, the dark green oil was obtained again. The small amount of ethanol was added and stirred for 2 min. Then the large amount of ethyl acetate was added. The green solid was precipitated immediately. After 3 hours at −20° C., the suspension was filtered off, with obtaining a green solid, which was washed with ethyl acetate, n-hexane, and dried under vacuum at 45° C. for 5 hrs to afford dark green powder as [$Mn_2(\mu-O)_2(\mu-CH_3COO)(Me_4$-DTNE)]$Cl_2 \cdot H_2O$.

8.1 Ethanol as Solvent

Ethanol: 10 mL: a green powder was isolated having a UV-Vis purity of 100%, and the yield of 96.3%.

UV-Vis spectrum ($\epsilon$: $mol^{-1} \cdot L \cdot cm^{-1}$, in water, Mw: 630): 271 nm (13332), 554 nm (317), 639 nm (327).

IR (KBr pellet): 3419 br, 2923m, 1606m, 1565m, 1499w, 1461s, 1396s, 1340m, 1288w, 1159w, 1076w, 1057w, 1036m, 1007m, 915w, 778w, 744w, 682w, 613m cm$^{-1}$.

UPLC analysis confirmed the trace amount of free [$H_2(Me_4$-DTNE)]$Cl_2$.

Water analysis (Karl-Fischer method): Anal. calcd. for [($Mn_2(\mu-O)_2(\mu-OAc)(Me_4$-DTNE)]$Cl_2 \cdot H_2O$: 2.86%. Found: 4.71%.

8.2 Methanol as Solvent

Methanol: 10 mL: a green powder was obtained showing UV-Vis purity of 99%, and the yield of 102.9%.

UV-Vis spectrum (ε: mol$^{-1}$·L·cm$^{-1}$, in water, Mw: 630): 271 nm (13388), 554 nm (308), 639 nm (318).

Anal. calcd. for [Mn$_2$O$_2$(CH$_3$COO)(C$_{18}$H$_{40}$N$_6$)]Cl$_2$.H$_2$O (C$_{20}$H$_{45}$Cl$_2$Mn$_2$N$_6$O$_5$): C, 38.11; H, 7.20; N, 13.33. Found: C, 38.33; H, 7.63; N, 12.57%.

IR (KBr pellet): 3425 br, 2923m, 1642m, 1568m, 1499w, 1462s, 1395s, 1337m, 1286w, 1159w, 1076m, 1055m, 1033m, 1004m, 912w, 780w, 744m, 678m, 613m cm$^{-1}$.

MS-ES$^+$: m/e 270.6.

UPLC analysis confirmed the trace amount of free [H$_2$(Me$_4$-DTNE)]Cl$_2$ in the Mn complex.

Total chloride amount was 11.07%.

Water analysis (Karl-Fischer method): Anal. calcd. for [(Mn$_2$(μ-O)$_2$(μ-OAc)(Me$_4$-DTNE)]Cl$_2$.H$_2$O: 2.86%. Found: 3.80%.

8.3 Dichloromethane as Solvent.

Dichloromethane: 20 mL: a green powder was obtaining of a UV-Vis purity of 101%, and the yield of 95.6%.

UV-Vis spectrum (ε: mol$^{-1}$·L·cm$^{-1}$, in water, Mw: 630): 271 nm (13114), 554 nm (314), 639 nm (340).

IR (KBr pellet): 3426 br, 2926m, 1636m, 1564s, 1499w, 1462s, 1397s, 1341m, 1288w, 1159w, 1076m, 1055m, 1038m, 1001m, 916w, 778w, 744m, 682m, 614m cm$^{-1}$.

UPLC analysis confirmed the trace amount of free [H$_2$(Me$_4$-DTNE)]Cl$_2$ in the Mn complex.

Total chloride amount was 10.19%.

Water analysis (Karl-Fischer method): Anal. calcd. for [(Mn$_2$(μ-O)$_2$(μ-OAc)(Me$_4$-DTNE)]Cl$_2$.H$_2$O: 2.86%. Found: 1.92%.

8.4 Acetonitrile as Solvent.

Acetonitrile: 10 mL: a green powder was isolated having a UV-Vis purity of 85.3%, and the isolated yield of 87.2%.

UV-Vis spectrum (ε: mol$^{-1}$·L·cm$^{-1}$, in water, Mw: 630): 271 nm (11345), 554 nm (265), 639 nm (280).

IR (KBr pellet): 3433 br, 2923m, 1642m, 1567m, 1499w, 1460m, 1396m, 1341w, 1058m, 1033m, 1004w, 912w, 780w, 744m, 678w, 613w cm$^{-1}$.

UPLC analysis confirmed the trace amount of free [H$_2$(Me$_4$-DTNE)]Cl$_2$ in the Mn complex.

Total chloride amount was 14.07%.

Water analysis (Karl-Fischer method): Anal. calcd. for [(Mn$_2$(μ-O)$_2$(μ-OAc)(Me$_4$-DTNE)]Cl$_2$.H$_2$O: 2.86%. Found: 1.39%.

8.5 Acetone as Solvent.

Acetone: 30 mL: yielding a green powder having a UV-Vis purity of 88.1%, and the isolated yield of 83.6%.

UV-Vis spectrum (ε: mol$^{-1}$·L·cm$^{-1}$, in water, Mw: 630): 271 nm (11977), 554 nm (289), 639 nm (266).

IR (KBr pellet): 3426 br, 2924m, 1635s, 1560s, 1499w, 1458s, 1395s, 1338m, 1286w, 1183w, 1075m, 1056m, 1033m, 1003m, 985m, 913w, 780w, 744m, 678m, 616m cm$^{-1}$.

UPLC analysis confirmed the trace amount of free [H$_2$(Me$_4$-DTNE)]Cl$_2$ in the Mn complex.

Total chloride amount was 9.49%.

Water analysis (Karl-Fischer method): Anal. calcd. for [(Mn$_2$(μ-O)$_2$(μ-OAc)(Me$_4$-DTNE)]Cl$_2$.H$_2$O: 2.86%. Found: 2.66%.

8.6 Tetrahydrofuran (THF) as Solvent.

THF: 40 mL: yielding a green powder of a UV-Vis purity of 70.8%, and the isolated yield of 62.3%.

UV-Vis spectrum (ε: mol$^{-1}$·L·cm$^{-1}$, in water, Mw: 630): 271 nm (8921), 554 nm (231), 639 nm (233).

IR (KBr pellet): 3422 br, 2924m, 1604s, 1567s, 1498w, 1463s, 1395s, 1337m, 1294w, 1159w, 1057m, 1032m, 1004m, 986m, 911w, 779w, 744w, 677m, 613m cm$^{-1}$.

UPLC analysis confirmed the trace amount of free [H$_2$(Me$_4$-DTNE)]Cl$_2$ in the Mn complex.

Total chloride amount was 10.51%.

Water analysis (Karl-Fischer method): Anal. calcd. for [(Mn$_2$(μ-O)$_2$(μ-OAc)(Me$_4$-DTNE)]Cl$_2$.H$_2$O: 2.86%. Found: 1.53%.

Example 9: Preparation of [(Mn$_2$(μ-O)$_2$(μ-OAc)(Me$_4$-DTNE)]Cl$_2$ Dissolved in an Organic Solution Under N$_2$, to Me$_4$-DTNE (95% purity, 4 mmol) in different solvents (10 mL to 20 mL), solid mixture of MnCl$_2$ (99% purity, 8.8 mmol) and sodium acetate (99% purity, 2 mmol) were added. The mixture was stirred for 30 min at 58° C. After another stirring for 10 min cooled in an ice water bath, the freshly prepared mixture of 1 M of H$_2$O$_2$ in water (9 mL, 9 mmol) and 5 M of NaOH (1.35 mL, 6.75 mmol) was added drop-wise over 10 min. The mixture turned immediately dark green-brown. The mixture was stirred for 20 min in an ice water bath and then for 20 min at room temperature. Glacial acetic acid (2.5 mmol) was added. After stirring for another 20 min, the mixture was filtered to remove brown solid and the filtering bed was washed with solvents. Then the mixture reached 20 mL to 40 mL by adding solvents. From this green solution, a 40 (or 50) times dilution and a 1600 (or 2000) times dilution were made; and from the absorption in the UV-Vis spectrum at the wavelengths of 244 nm, 554 nm, and 639 nm, the concentration in the stock and the conversion were calculated, based on the molar extinction coefficient of [Mn$_2$(μ-O)$_2$(μ-OAc)(Me$_4$-DTNE)]Cl$_2$ with Mw 612) in water for 100% pure, ε (mol$^{-1}$·L·cm$^{-1}$): 271 nm (13200 mol$^{-1}$·L·cm$^{-1}$), 554 nm (315 mol$^{-1}$·L·cm$^{-1}$), 639 nm (325 mol$^{-1}$·L·cm$^{-1}$).

10.1 Ethylene Glycol as Solvent.

Ethylene glycol: 10 mL; the volume of the solution contained catalyst: 28 mL; diluted times: 50 times and 2000 times; UV-vis extinction:

271 nm: 1.052
554 nm: 0.905
639 nm: 0.869

So, the average UV-Vis conversion was 101.4%; the solution contained 8.01% (wt %) of the catalyst with the density of 1.112 g/mL.

UPLC analysis confirmed the trace amount of free [H$_2$(Me$_4$-DTNE)]Cl$_2$ in the Mn complex.

Total chloride amount was 1.89%.

10.2 1,2-Propylene Glycol as Solvent.

1,2-Propylene glycol: 10 mL; the volume of the solution contained catalyst: 40 mL; diluted times: 40 times and 1600 times; UV-vis extinction:

271 nm: 0.937
554 nm: 0.832
639 nm: 0.860

So, the average UV-Vis conversion was 107.1%; the solution contained 6.18% (wt %) of the catalyst with the density of 1.074 g/mL.

UPLC analysis confirmed the trace amount of free [H$_2$(Me$_4$-DTNE)]Cl$_2$ in the Mn complex.

Total chloride amount was 1.35%.

10.3 1,3-Propylene Glycol as Solvent.

1,3-Propylene glycol: 10 mL; the volume of the solution contained catalyst: 35 mL; diluted times: 40 times and 1600 times; UV-vis extinction:

271 nm: 1.048
554 nm: 0.990
639 nm: 1.040

So, the average UV-Vis conversion was 110.5%; the solution contained 7.23% (wt %) of the catalyst with the density of 1.075 g/mL.

UPLC analysis confirmed the trace amount of free [H$_2$(Me$_4$-DTNE)]Cl$_2$ in the Mn complex.

Total chloride amount was 1.60%.

10.4 Dimethyl Formamide (DMF) as Solvent.

DMF: 10 mL; the volume of the solution contained catalyst: 30 mL; diluted times: 40 times and 1600 times; UV-vis extinction:
271 nm: 1.295
554 nm: 1.152
639 nm: 1.120

So, the average UV-Vis conversion was 109.4%; the solution contained 8.66% (wt %) of the catalyst with the density of 1.039 g/mL.

UPLC analysis confirmed the trace amount of free [H$_2$(Me$_4$-DTNE)]Cl$_2$ in the Mn complex.

Total chloride amount was 1.80%.

10.5 Dimethyl Sulfoxide (DMSO) as Solvent.

DMSO: 20 mL; the volume of the solution contained catalyst: 40 mL; diluted times: 40 times and 1600 times; UV-vis extinction:
271 nm: 0.625
554 nm: 0.744
639 nm: 0.680

So, the average UV-Vis conversion was 82.9%; the solution contained 4.60% (wt %) of the catalyst with the density of 1.125 g/mL.

UPLC analysis confirmed the trace amount of free [H$_2$(Me$_4$-DTNE)]Cl$_2$ in the [Mn$_2$(μ-O)$_2$(μ-OAc)(Me$_4$-DTNE)]Cl$_2$ solutions.

Total chloride amount was 1.12%.

The solvents, ethylene glycol, 1,2-propylene glycol and 1,3-propylene glycol can be readily used to mix with other solutions (e.g. water, surfactant containing formulations, for various applications, such as domestic and industrial cleaning, textile treatment, etc.

Example 11: Preparation of [Mn$_2$(μ-O)$_2$(μ-OAc)(Me$_4$-DTNE)]Cl$_2$ Complexation in Non-Aqueous Solutions, Isolation in Aqueous Solutions Under N$_2$, to Me$_4$-DTNE (95% purity, 4 mmol) in different solvents, solid mixture of MnCl$_2$ (99% purity, 8.8 mmol) and sodium acetate (99% purity, 2 mmol) were added. The mixture was stirred for 30 min at 58° C. for toluene or 40° C. for CH$_2$Cl$_2$. The mixture was then cooled in an ice water bath and stirred for another 10 min. The freshly prepared mixture of 1 M of H$_2$O$_2$ in water (9 mL, 9 mmol) and 5 M of NaOH (1.35 mL, 6.75 mmol) was added drop-wise over 10 min. The mixture turned immediately dark green-brown. The mixture was stirred for 20 min in an ice water bath and then for 20 min at room temperature. Glacial acetic acid (2.5 mmol) was added. After stirring for another 20 min, the mixture was filtered to remove brown solid and the filtering bed was washed with water. The filtrate divided into two layers. The water layer was then separated directly through a separating funnel. Trace volatile was removed for 20 min in vacuum. The mixture reached 25 mL by adding millipore water. From this green solution, a 50 times dilution and a 2000 times dilution were made; and from the absorption in the UV-Vis spectrum at the wavelengths of 244 nm, 554 nm, and 639 nm, the concentration in the stock and the conversion were calculated, based on the molar extinction coefficient of [(Mn$_2$(μ-O)$_2$(μ-OAc)(Me$_4$-DTNE)]Cl$_2$ with Mw 612 in water for 100% pure, ε (mol$^{-1}$·L·cm$^{-1}$): 271 nm (13200 mol$^{-1}$·L·cm$^{-1}$), 554 nm (315 mol$^{-1}$·L·cm$^{-1}$), 639 nm (325 mol$^{-1}$·L·cm$^{-1}$).

11.1 Toluene as Solvent.

Toluene: 30 mL; the volume of the solution contained catalyst: 25 mL; diluted times: 50 times and 2000 times; UV-vis extinction:
271 nm: 0.924
554 nm: 0.883
639 nm: 0.901

So, the average UV-Vis conversion was 86.1%; the aqueous solution contained 8.21% (wt %) of the catalyst with the density of 1.041 g/mL.

UPLC analysis confirmed the trace amount of free [H$_2$(Me$_4$-DTNE)]Cl$_2$.

Total chloride amount was 2.19%.

11.2 Dichloromethane as Solvent.

CH$_2$Cl$_2$: 30 mL; the volume of the solution contained catalyst: 25 mL; diluted times: 50 times and 2000 times; UV-vis extinction:
271 nm: 1.162
554 nm: 1.059
639 nm: 1.090

So, the average UV-Vis conversion was 106.4%; the aqueous solution contained 10.43% (wt %) of the catalyst with the density of 1.043 g/mL.

UPLC analysis confirmed the trace amount of free [H$_2$(Me$_4$-DTNE)]Cl$_2$.

Total chloride amount was 2.51%.

Example 12: Preparation of Solid [Mn$_2$(μ-O)$_2$(μ-OAc)(Me$_4$-DTNE)](PF$_6$)$_2$ Under N$_2$, to Me$_4$-DTNE (95% purity, 10 mmol) in solvents, solid mixture of MnCl$_2$·4H$_2$O (22 mmol) and NaAc (5 mmol) were added. The mixture was stirred for 30 min at 58° C. After another stirring for 10 min cooled in an ice water bath, the freshly prepared mixture of 1 M of H$_2$O$_2$ in water (22.5 mL, 22.5 mmol) and 5 M of NaOH (3.375 mL, 16.875 mmol) was added drop-wise over 5 min. The mixture turned immediately dark green-brown. The mixture was then stirred for 20 min in an ice water bath and then for 20 min at room temperature. Glacial acetic acid (6.25 mmol) was added. After stirring for another 20 min, an aqueous of KPF$_6$ (30 mmol) in 75 mL of mQ water was added. 50 mL of acetonitrile was added to dissolve the green precipitate 5 min later. After stirring for another 10-15 min, the mixture was filtered to remove brown solid and the filtering bed was washed with acetonitrile. Then the mixture reached 260 mL or 170 mL by adding acetonitrile. All solvents in the green solution were evaporated (the water bath temperature <45° C.). The dark green residue was coevaporated with ethanol and ethyl acetate to facilitate the removal of most of the remaining water. The dark green residue was taken up in acetonitrile (125 mL), and the insoluble white salts separated by filtration were washed with acetonitrile. The partial evaporation of acetonitrile, water (50 mL) was added, and then the remainder of acetonitrile evaporated to leave a green solid and a little bit water. The suspension was put in a −25° C. fridge overnight, and was filtered off. The green solid was washed with cold water, ethanol, and n-hexane, and dried under vacuum at 45° C. for 5 hrs to afford dark green powder as [(Mn$_2$(μ-O)$_2$(μ-OAc)(Me$_4$-DTNE)](PF$_6$)$_2$.

12.1 EtOH/H$_2$O (2:1, v/v) as Solvent (Benchmark, Procedure According to Prior Art)

Ethanol/water (2:1, v/v): 100 mL. Green powder isolated, UV-Vis purity of 95.9%, and the isolated yield of 72.3%.

UV-Vis spectrum (ε: mol$^{-1}$·L·cm$^{-1}$, in acetonitrile, Mw 831): 271 nm (15442), 554 nm (342), 639 nm (387).

Anal. calcd. for $C_{20}H_{43}F_{12}Mn_2N_6O_4P_2$: C, 28.89; H, 5.21; N, 10.11. Found: C, 28.79; H, 5.21; N, 10.25%.

IR (KBr pellet): 3441 br, 2933m, 1633m, 1561m, 1499w, 1467m, 1384m, 1341m, 1287w, 1159w, 1077m, 1057m, 1035m, 1005m, 985m, 840vs, 780w, 743w, 692m, 679m, 608m, 558m cm$^{-1}$.

UPLC analysis confirmed the trace amount of free [H$_2$(Me$_4$-DTNE)](PF$_6$)$_2$.

The water amount was 1.78% by Karl-Fischer method.

12.2 Ethanol as Solvent.

Ethanol: 25 mL; green powder isolated, UV-Vis purity of 98.6%, and the isolated yield of 85.9%.

UV-Vis spectrum (ε: mol$^{-1}$·L·cm$^{-1}$, in acetonitrile, Mw: 831): 271 nm (16041), 554 nm (351), 639 nm (396).

Anal. calcd. for $C_{20}H_{43}F_{12}Mn_2N_6O_4P_2$: C, 28.89; H, 5.21; N, 10.11. Found: C, 28.77; H, 5.22; N, 10.19%.

IR (KBr pellet): 3441 br, 2933m, 1633m, 1562m, 1499w, 1467m, 1384m, 1342m, 1287w, 1159w, 1078m, 1058m, 1036m, 1005m, 986m, 840vs, 780w, 743w, 692m, 679m, 608m, 558m cm$^{-1}$.

MS-ES$^+$: m/e 270.6.

UPLC analysis confirmed the trace amount of free [H$_2$(Me$_4$-DTNE)](PF$_6$)$_2$.

The water amount was 0.55% by Karl-Fischer method.

Example 13: Preparation of [Mn$_2$(μ-O)$_3$(Me$_3$-TACN)]Cl$_2$.3H$_2$O

Under N$_2$, the mixture of Me$_3$-TACN (99% purity, 10 mmol), manganese(II)chloride (11 mmol) in either 20 mL water (6.1) or 20 mL ethanol (6.2) was stirred for 20 min at 35° C. After another stirring for 10 min cooled in an ice water bath, a freshly prepared mixture of 1 M H$_2$O$_2$ (12.5 mmol) and 5 M NaOH (15 mmol) was added dropwise over 5-10 min. The mixture turned immediately dark brown/red. The mixture was further stirred for 20 min in an ice bath and for another 40 min at room temperature. 1 M HCl (5.2 mmol) was added and stirred for 30 min in order to adjust pH value to 5. The red-wine mixture was filtered to remove brown solid and the filtering bed was washed with ethanol. The filtrate was reduced in vacuo (water bath: 35° C.-40° C.) to afford a red-oil. The residue was dissolved in ethanol, and the insoluble white salts separated by filtration were washed with ethanol. The ethanol filtrate combined was evaporated to dryness obtaining a red-oil. The red-oil was washed with acetonitrile and ethyl acetate until obtaining red solid, which was dried in vacuum at 45° C. for 6 hrs to afford red solid as [Mn$_2$(μ-O)$_3$(Me$_3$-TACN)$_2$]Cl$_2$.3H$_2$O.

13.1: Water as Complexation Solvent

Red powder, UV-Vis purity of 92.7%, and the yield of 88%.

UV-Vis spectrum (ε: mol$^{-1}$·L·cm$^{-1}$, in water, Mw 625): 244 nm (18016), 278 nm (17190), 313 nm (11069), 389 nm (949), 485 nm (355).

UPLC analysis confirmed the trace amounts of free [H$_2$(Me$_3$-TACN)]Cl$_2$.

Total chloride amount was 12.35%.

13.2 Ethanol as Complexation Solvent

Red powder, UV-Vis purity of 92.9%, and the yield of 82%.

UV-Vis spectrum (ε: mol$^{-1}$·L·cm$^{-1}$, in water, Mw 625): 244 nm (18048), 278 nm (17231), 313 nm (11113), 389 nm (979), 485 nm (370).

UPLC analysis confirmed the trace amounts of free [H$_2$(Me$_3$-TACN)]Cl$_2$.

Total chloride amount was 11.83%.

The results shown in sections 6.1 and 6.2 indicated that both solvents (aqueous vs non-aqueous solvents) are suitable to form complex, whilst the non-aqueous solvent exhibits the advantage that the non-aqueous solvent may be easier removed by evaporated than the aqueous solvent.

The invention claimed is:

1. A powder obtained by spray-drying or freeze-drying, consisting of
   (a) a manganese transition metal catalyst of a ligand and a non-coordinating counterion of the manganese transition metal catalyst, wherein the ligand is selected from 1,4,7-trimethyl-1,4,7-triazacyclononane (Me$_3$-TACN) and 1,2-bis-(4,7-dimethyl-1,4,7-triazacyclonon-1-yl)-ethane (Me$_4$-DTNE), and wherein the non-coordinating counterion is selected from the group consisting of chloride, bromide, sulfate, nitrate, acetate, and benzoate,
   (b) less than 14 wt % of water,
   (c) between 5 and 95 wt % of an inert salt, and
   (d) minor impurities.

2. The powder of claim 1, which comprises less than 12 wt % water.

3. The powder of claim 1, which comprises less than 10 wt % water.

4. The powder of claim 1, which comprises less than 6 wt % water.

5. The powder of claim 1, wherein the inert salt is NaCl.

6. The powder of claim 5, which comprises between 25 and 75 wt % NaCl.

7. The powder of claim 1, wherein the catalyst is a salt of the metal complexes [(Mn$^{IV}$)$_2$(m-O)$_3$(Me$_3$-TACN)$_2$]$^{2+}$, [(Mn$^{III}$)$_2$(m-O)(m-CH$_3$COO)$_2$(Me$_3$-TACN)$_2$)]$^{2+}$ or [Mn$^{III}$Mn$^{IV}$(m-O)$_2$(m-CH$_3$COO)(Me$_4$-DTNE)]$^{2+}$.

8. The powder of claim 1, wherein the non-coordinating counterion is selected to provide a preformed transition-metal catalyst that has a water solubility of at least 30 g/l at 20° C.

9. The powder of claim 1, wherein the catalyst is selected from the group consisting of [(Mn$^{IV}$)$_2$(m-O)$_3$(Me$_3$-TACN)$_2$]SO$_4$, [Mn$^{III}$Mn$^{IV}$(m-O)$_2$(m-CH$_3$COO)(Me$_4$-DTNE)]Cl$_2$, [(Mn$^{IV}$)$_2$(m-O)$_3$(Me$_3$-TACN)$_2$](CH$_3$COO)$_2$, [(Mn$^{IV}$)$_2$(m-O)$_3$(Me$_3$-TACN)$_2$](NO$_3$)$_2$ and [Mn$^{III}$Mn$^{IV}$(m-O)$_2$(m-CH$_3$COO)(Me$_4$-DTNE)](NO$_3$)$_2$.

10. The powder of claim 1, wherein the catalyst is [(Mn$^{IV}$)$_2$(m-O)$_3$(Me$_3$-TACN)$_2$]SO$_4$.

11. The powder of claim 1, wherein the catalyst is [Mn$^{III}$Mn$^{IV}$(m-O)$_2$(m-CH$_3$COO)(Me$_4$-DTNE)]Cl$_2$.

12. A method of preparing the powder of claim 1, the method comprising spray-drying or freeze-drying a mixture comprising the catalyst, wherein the mixture comprises more than 20% water.

13. The method of claim 1 wherein the powder comprises less than 12 wt % water.

14. The method of claim 1 wherein the method further comprises synthesizing the catalyst, prior to the spray-drying or freeze-drying, in which a complexation between manganese ion(s) and the ligand of formula (I) is effected in a complexation mixture comprising more than 6 wt % of water.

15. The method of claim 1, wherein the catalyst is a salt of [(Mn$^{IV}$)$_2$(m-O)$_3$(Me$_3$-TACN)$_2$]$^{2+}$, [(Mn$^{III}$)$_2$(m-O)(m-CH$_3$COO)$_2$(Me$_3$-TACN)$_2$)]$^{2+}$ or [Mn$^{III}$Mn$^{IV}$(m-O)$_2$(m-CH$_3$COO)(Me$_4$-DTNE)]$^{2+}$.

16. The method of claim 1, wherein the catalyst has a non-coordinating counterion selected to provide a preformed transition-metal catalyst that has a water solubility of at least 30 g/l at 20° C.

17. The method of claim 1, wherein the catalyst is selected from the group consisting of $[(Mn^{IV})_2(m-O)_3(Me_3\text{-}TACN)_2]SO_4$, $[Mn^{III}Mn^{IV}(m-O)_2(m-CH_3COO)(Me_4\text{-}DTNE)]Cl_2$, $[(Mn^{IV})_2(m-O)_3(Me_3\text{-}TACN)_2](CH_3COO)_2$, $[(Mn^{IV})_2(m-O)_3(Me_3\text{-}TACN)_2](NO_3)_2$ and $[Mn^{III}Mn^{IV}(m-O)_2(m-CH_3COO)(Me_4\text{-}DTNE)](NO_3)_2$.

18. The method of claim 17, wherein the catalyst is $[(Mn^{IV})_2(m-O)_3(Me_3\text{-}TACN)_2]SO_4$.

19. The method of claim 17, wherein the catalyst is $[Mn^{III}Mn^{IV}(m-O)_2(m-CH_3COO)(Me_4\text{-}DTNE)]Cl_2$.

20. The method of claim 1, wherein the spray-drying or freeze-drying is of an aqueous mixture.

21. The method of claim 1, wherein the spray-drying or freeze-drying is of a solution.

22. The method of claim 1, wherein the powder is further dried under reduced pressure after spray-drying or freeze-drying, so that the resultant powder comprises less than 10 wt % water.

23. The method claim 22, wherein the resultant powder comprises less than 6 wt % water.

24. The method of claim 1, wherein the mixture is spray-dried and the spray-drying comprises:

(a) dispersing the mixture of the transition metal catalyst comprising in the form of drops into a spraying tower, and (b) supplying a hot gas at a temperature between about 70° C. and about 150° C. into the spraying tower, and having an outlet temperature comprised between about 20° C. and about 90° C., whereby to provide the spray-dried powder.

25. The method of claim 1, wherein the mixture that is spray-dried further comprises an inorganic salt.

26. The method of claim 25, wherein the salt is selected from the group consisting of citrate, chloride, phosphate, sulfate, acetate salts of sodium, potassium, calcium, and magnesium.

27. The method of claim 25, wherein the salt is sodium chloride.

* * * * *

UNITED STATES PATENT AND TRADEMARK OFFICE
CERTIFICATE OF CORRECTION

| | | |
|---|---|---|
| PATENT NO. | : 10,144,005 B2 | Page 1 of 2 |
| APPLICATION NO. | : 14/343174 | |
| DATED | : December 4, 2018 | |
| INVENTOR(S) | : Richard William Kemp et al. | |

It is certified that error appears in the above-identified patent and that said Letters Patent is hereby corrected as shown below:

In the Claims

At Column 26, Claim 7, Lines 35-37, replace
"$[(Mn^{IV})_2(m\text{-}O)_3(Me_3\text{-}TACN)_2]^{2+}$, $[(Mn^{III})_2(m\text{-}O)(m\text{-}CH_3COO)_2(Me_3\text{-}TACN)_2)]^{2+}$ or $[Mn^{III}Mn^{IV}(m\text{-}O)_2(m\text{-}CH_3COO)(Me_4\text{-}DTNE)]^{2+}$" with
-- $[(Mn^{IV})_2(\mu\text{-}O)_3(Me_3\text{-}TACN)_2]^{2+}$, $[(Mn^{III})_2(\mu\text{-}O)(\mu\text{-}CH_3COO)_2(Me_3\text{-}TACN)_2)]^{2+}$ or $[Mn^{III}Mn^{IV}(\mu\text{-}O)_2(\mu\text{-}CH_3COO)(Me_4\text{-}DTNE)]^{2+}$ --.

At Column 26, Claim 8, Line 40, replace "30 g/I" with -- 30 g/l --.

At Column 26, Claim 9, Lines 43-47, replace
"$[(Mn^{IV})_2(m\text{-}O)_3(Me_3\text{-}TACN)_2]SO_4$, $[Mn^{III}Mn^{IV}(m\text{-}O)_2(m\text{-}CH_3COO)(Me_4\text{-}DTNE)]Cl_2$, $[(Mn^{IV})_2(m\text{-}O)_3(Me_3\text{-}TACN)_2](CH_3COO)_2$, $[(Mn^{IV})_2(m\text{-}O)_3(Me_3\text{-}TACN)_2](NO_3)_2$ and $[Mn^{III}Mn^{IV}(m\text{-}O)_2(m\text{-}CH_3COO)(Me_4\text{-}DTNE)](NO_3)_2$" with
-- $[(Mn^{IV})_2(\mu\text{-}O)_3(Me_3\text{-}TACN)_2]SO_4$, $[Mn^{III}Mn^{IV}(\mu\text{-}O)_2(\mu\text{-}CH_3COO)(Me_4\text{-}DTNE)]Cl_2$, $[(Mn^{IV})_2(\mu\text{-}O)_3(Me_3\text{-}TACN)_2](CH_3COO)_2$, $[(Mn^{IV})_2(\mu\text{-}O)_3(Me_3\text{-}TACN)_2](NO_3)_2$ and $[Mn^{III}Mn^{IV}(\mu\text{-}O)_2(\mu\text{-}CH_3COO)(Me_4\text{-}DTNE)](NO_3)_2$ --.

At Column 26, Claim 10, Line 49, replace "$[(Mn^{IV})_2(m\text{-}O)_3(Me_3\text{-}TACN)_2]SO_4$" with
-- $[(Mn^{IV})_2(\mu\text{-}O)_3(Me_3\text{-}TACN)_2]SO_4$ --.

At Column 26, Claim 11, Line 51, replace "$[Mn^{III}Mn^{IV}(m\text{-}O)_2(m\text{-}CH_3COO)(Me_4\text{-}DTNE)]Cl_2$" with
-- $[Mn^{III}Mn^{IV}(\mu\text{-}O)_2(\mu\text{-}CH_3COO)(Me_4\text{-}DTNE)]Cl_2$ --.

At Column 26, Claim 13, Line 56, replace "claim 1" with -- claim 12 --.

At Column 26, Claim 14, Line 58, replace "claim 1" with -- claim 12 --.

At Column 26, Claim 15, Line 64, replace "claim 1" with -- claim 12 --.

Signed and Sealed this
Twenty-fourth Day of March, 2020

Andrei Iancu
*Director of the United States Patent and Trademark Office*

At Column 26, Claim 15, Lines 65-67, replace
"[(Mn$^{IV}$)$_2$(m-O)$_3$(Me$_3$-TACN)$_2$]$^{2+}$, [(Mn$^{III}$)$_2$(m-O)(m-CH$_3$COO)$_2$(Me$_3$-TACN)$_2$)]$^{2+}$ or [Mn$^{III}$Mn$^{IV}$(m-O)$_2$(m-CH$_3$COO)(Me$_4$-DTNE)]$^{2+}$" with
-- [(Mn$^{IV}$)$_2$(µ-O)$_3$(Me$_3$-TACN)$_2$]$^{2+}$, [(Mn$^{III}$)$_2$(µ-O)(µ-CH$_3$COO)$_2$(Me$_3$-TACN)$_2$)]$^{2+}$ or [Mn$^{III}$Mn$^{IV}$(µ-O)$_2$(µ-CH$_3$COO)(Me$_4$-DTNE)]$^{2+}$ --.

At Column 27, Claim 16, Line 1, replace "claim 1" with -- claim 12 --.

At Column 27, Claim 16, Line 4, replace "30 g/I" with -- 30 g/l --.

At Column 27, Claim 17, Line 5, replace "claim 1" with -- claim 12 --.

At Column 27, Claim 17, Lines 6-10, replace
"[(Mn$^{IV}$)$_2$(m-O)$_3$(Me$_3$-TACN)$_2$]SO$_4$, [Mn$^{III}$Mn$^{IV}$(m-O)$_2$(m-CH$_3$COO)(Me$_4$-DTNE)]Cl$_2$, [(Mn$^{IV}$)$_2$(m-O)$_3$(Me$_3$-TACN)$_2$](CH$_3$COO)$_2$, [(Mn$^{IV}$)$_2$(m-O)$_3$(Me$_3$-TACN)$_2$](NO$_3$)$_2$ and [Mn$^{III}$Mn$^{IV}$(m-O)$_2$(m-CH$_3$COO)(Me$_4$-DTNE)](NO$_3$)$_2$" with
-- [(Mn$^{IV}$)$_2$(µ-O)$_3$(Me$_3$-TACN)$_2$]SO$_4$, [Mn$^{III}$Mn$^{IV}$(µ-O)$_2$(µ-CH$_3$COO)(Me$_4$-DTNE)]Cl$_2$, [(Mn$^{IV}$)$_2$(µ-O)$_3$(Me$_3$-TACN)$_2$](CH$_3$COO)$_2$, [(Mn$^{IV}$)$_2$(µ-O)$_3$(Me$_3$-TACN)$_2$](NO$_3$)$_2$ and [Mn$^{III}$Mn$^{IV}$(µ-O)$_2$(µ-CH$_3$COO)(Me$_4$-DTNE)](NO$_3$)$_2$ --.

At Column 27, Claim 18, Line 12, replace "[(Mn$^{IV}$)$_2$(m-O)$_3$(Me$_3$-TACN)$_2$]SO$_4$" with
-- [(Mn$^{IV}$)$_2$(µ-O)$_3$(Me$_3$-TACN)$_2$]SO$_4$ --.

At Column 27, Claim 19, Line 14, replace "[Mn$^{III}$Mn$^{IV}$(m-O)$_2$(m-CH$_3$COO)(Me$_4$-DTNE)]Cl$_2$" with
-- [Mn$^{III}$Mn$^{IV}$(µ-O)$_2$(µ-CH$_3$COO)(Me$_4$-DTNE)]Cl$_2$ --.

At Column 27, Claim 20, Line 15, replace "claim 1" with -- claim 12 --.

At Column 27, Claim 21, Line 17, replace "claim 1" with -- claim 12 --.

At Column 27, Claim 22, Line 19, replace "claim 1" with -- claim 12 --.

At Column 28, Claim 24, Line 3, replace "claim 1" with -- claim 12 --.

At Column 28, Claim 25, Line 13, replace "claim 1" with -- claim 12 --.